(12) United States Patent
Branham et al.

(10) Patent No.: US 7,479,535 B2
(45) Date of Patent: Jan. 20, 2009

(54) PHOSPHOROUS-CONTAINING COMPOUNDS WITH POLYMERIC CHAINS, AND METHODS OF MAKING AND USING THE SAME

(75) Inventors: Keith Branham, Pelham, AL (US); Mahesh V. Chaubal, Ellicott City, MD (US); James P. English, Chelsea, AL (US); Donna Hall, Verbena, AL (US); Zhong Zhao, Ellicott City, MD (US)

(73) Assignee: Guilford Pharmaceuticals, Inc., Baltimore, MD (US)

( * ) Notice: Subject to any disclaimer, the term of this patent is extended or adjusted under 35 U.S.C. 154(b) by 523 days.

(21) Appl. No.: 10/505,529

(22) PCT Filed: Feb. 25, 2003

(86) PCT No.: PCT/US03/05795
§ 371 (c)(1),
(2), (4) Date: Apr. 12, 2005

(87) PCT Pub. No.: WO03/080629
PCT Pub. Date: Oct. 2, 2003

(65) Prior Publication Data
US 2005/0182236 A1 Aug. 18, 2005

Related U.S. Application Data

(60) Provisional application No. 60/359,314, filed on Feb. 25, 2002.

(51) Int. Cl.
C08G 79/02 (2006.01)
C08G 79/04 (2006.01)
C08G 79/00 (2006.01)

(52) U.S. Cl. .............. 528/398; 528/399; 528/422; 528/425

(58) Field of Classification Search ............ 528/398, 528/425, 422, 399
See application file for complete search history.

(56) References Cited

U.S. PATENT DOCUMENTS

| 3,442,982 A | 5/1969 | Friedman et al. |
| 5,256,765 A | 10/1993 | Leong |
| 5,278,201 A | 1/1994 | Dunn et al. |

(Continued)

FOREIGN PATENT DOCUMENTS

EP 0 193 019 B1 9/1986

(Continued)

OTHER PUBLICATIONS

Choi et al., "Stair-Shaped Poly(ether-ester) Block Copolymers: Synthesis, Characterization, and Their Physical Properties," Macromolecules 31:8766-8774 (1998).

(Continued)

Primary Examiner—Duc Truong
(74) Attorney, Agent, or Firm—Foley Hoag LLP

(57) ABSTRACT

The present invention relates to novel phosphorus-containing compounds with polymeric chains, and methods of making and using the same. In part, subject compositions containing phosphorus-containing compounds with polymeric chains and a therapeutic agent, and methods of making and using the same, are described. Certain of the subject compositions exhibit reverse thermal gelation.

20 Claims, 2 Drawing Sheets

U.S. PATENT DOCUMENTS

| | | | |
|---|---|---|---|
| 5,278,202 A | 1/1994 | Dunn et al. |
| 5,324,519 A | 6/1994 | Dunn et al. |
| 5,340,849 A | 8/1994 | Dunn et al. |
| 5,368,859 A | 11/1994 | Dunn et al. |
| 5,487,897 A | 1/1996 | Polson et al. |
| 5,530,093 A | 6/1996 | Engelhardt et al. |
| 5,599,552 A | 2/1997 | Dunn et al. |
| 5,632,727 A | 5/1997 | Tipton et al. |
| 5,681,873 A | 10/1997 | Norton et al. |
| 5,702,716 A | 12/1997 | Dunn et al. |
| 5,702,717 A | 12/1997 | Cha et al. |
| 5,725,491 A | 3/1998 | Tipton et al. |
| 5,733,950 A | 3/1998 | Dunn et al. |
| 5,736,152 A | 4/1998 | Dunn |
| 5,739,176 A | 4/1998 | Dunn et al. |
| 5,744,153 A | 4/1998 | Yewey et al. |
| 5,747,058 A | 5/1998 | Tipton et al. |
| 5,759,563 A | 6/1998 | Yewey et al. |
| 5,780,044 A | 7/1998 | Yewey et al. |
| 5,792,469 A | 8/1998 | Tipton et al. |
| 5,888,533 A | 3/1999 | Dunn |
| 5,945,115 A | 8/1999 | Dunn et al. |
| 5,962,006 A | 10/1999 | Southard et al. |
| 5,968,542 A | 10/1999 | Tipton |
| 5,990,194 A | 11/1999 | Dunn et al. |
| 6,004,573 A | 12/1999 | Rathi et al. |
| 6,008,318 A | 12/1999 | Zhao et al. |
| 6,051,558 A | 4/2000 | Burns et al. |
| 6,117,949 A | 9/2000 | Rathi et al. |
| 6,120,789 A | 9/2000 | Dunn |
| 6,143,314 A | 11/2000 | Chandrashekar et al. |
| 6,201,072 B1 | 3/2001 | Rathi et al. |

FOREIGN PATENT DOCUMENTS

| | | |
|---|---|---|
| EP | 0 193 019 B2 | 9/1986 |
| EP | 0 269 105 A2 | 6/1988 |
| EP | 0 386 757 A2 | 9/1990 |
| EP | 0 493 927 | 7/1992 |
| EP | 0 989 162 | 3/2000 |
| GB | 2 198 135 | 6/1988 |
| WO | WO 97/40085 | 10/1997 |
| WO | WO 98/44020 | 10/1998 |
| WO | WO 99/50356 | 10/1999 |
| WO | WO 99/65531 | 12/1999 |
| WO | WO 00/57852 | 10/2000 |
| WO | WO 02/05800 | 1/2002 |

OTHER PUBLICATIONS

Fu et al., "Studies on the Melt Copolymerization of Phosphorus-Containing Diacid and BIS (p-Carboxyphenoxy) Propand for DDS," J. Wuhan Univ. (Natural Science Edition), 43(4):467-470 (1997).

Fu et al., "Studies on the Syntheses and Drug Release Properties of Polyanhydrides Containing Phosphonoformic (or Acetic) Acid Ethyl Ester in the Main Chain," Chemical Journal of Chinese Universities, 18(10)1706-1710 (1997).

Fu et al., "Studies on the Syntheses and Properties of Phosphorus-Containing Polyanhydrides for DDS," Chemical Journal of Chinese Universities, 18(5):813-817 (1997).

Ha et al., "Poly(ethylene oxide)-poly(propylene oxide)-poly(ethylene oxide) (Pluronic)/poly (ε-caprolactone) (PCL) amphiphilic block copolymeric nanospheres I. Preparation and Characterization," Journal of Controlled Release 62:381-392 (1999).

Jeong et al., "Biodegradable block copolymers as injectable drug-delivery systems," Nature 388:860-862 (Aug. 1997).

Jeong et al., "Biodegradable thermosensitive micelles of PEG-PLGA-PEG triblock copolymers," Colloids and Surfaces B: Biointerfaces 16:185-193 (1999).

Jeong et al., "Drug release from biodegradable injectable thermosensitive hydrogel of PEG-PLGA-PEG triblock copolymers," Journal of Controlled Release 63:155-163 (2000).

Jeong et al., "New biodegradable polymers for injectable drug delivery systems," Journal of Controlled Release 62:109-114 (1999).

Jeong et al., "Thermorever-sible Gelation of PEG-PLGA-PEB Triblock Copolymer Aqueous Solutions," Macromolecules 32:7064-7069 (1999).

Kadiyala et al., "Poly(phosphoesters): Synthesis, Physicochemical Characterization and Biological Response," Biomedical Applications of Synthetic Biodegradable Polymers, Chapter 3: 33-57, (Jeffrey O. Hollinger ed., 1995).

Kim et al., "In vivo evaluation of polymeric micellar paclitaxel formulation: toxicity and efficacy," Journal of Controlled Release 72:191-202 (2001).

Liu et al., "Synthesis of Phosphatidyl Ethanolamine Polyphosphate Liposomal Materials," Chemical Journal of Chinese Universities, 18(9):1556-1559 (1997).

Penczek et al., Synthetic Poly(Phosphates) Related to Nucleic and Teichoic Acids, Progress in Biomedical Polymers pp. 291-309 (1990).

Penczek et al., "High-Molecular-Weight Poly(alkylene phosphate)s and Preparation of Amphiphilic Polymers Thereof," Macromolecules 26:2228-2233 (1993).

Suh et al., "Regulation of Smooth Muscle Cell Proliferation Using Paclitaxel-Loaded Poly(ethylene oxide)-poly(lactide/glycolide) Nanospheres," J. Biomed. Mater. Res., 42(2):331-8 (1998).

Von Recum et al., "Growth factor release from thermally reversible tissue culture substrates," Journal of Controlled Release 55:121-130 (1998).

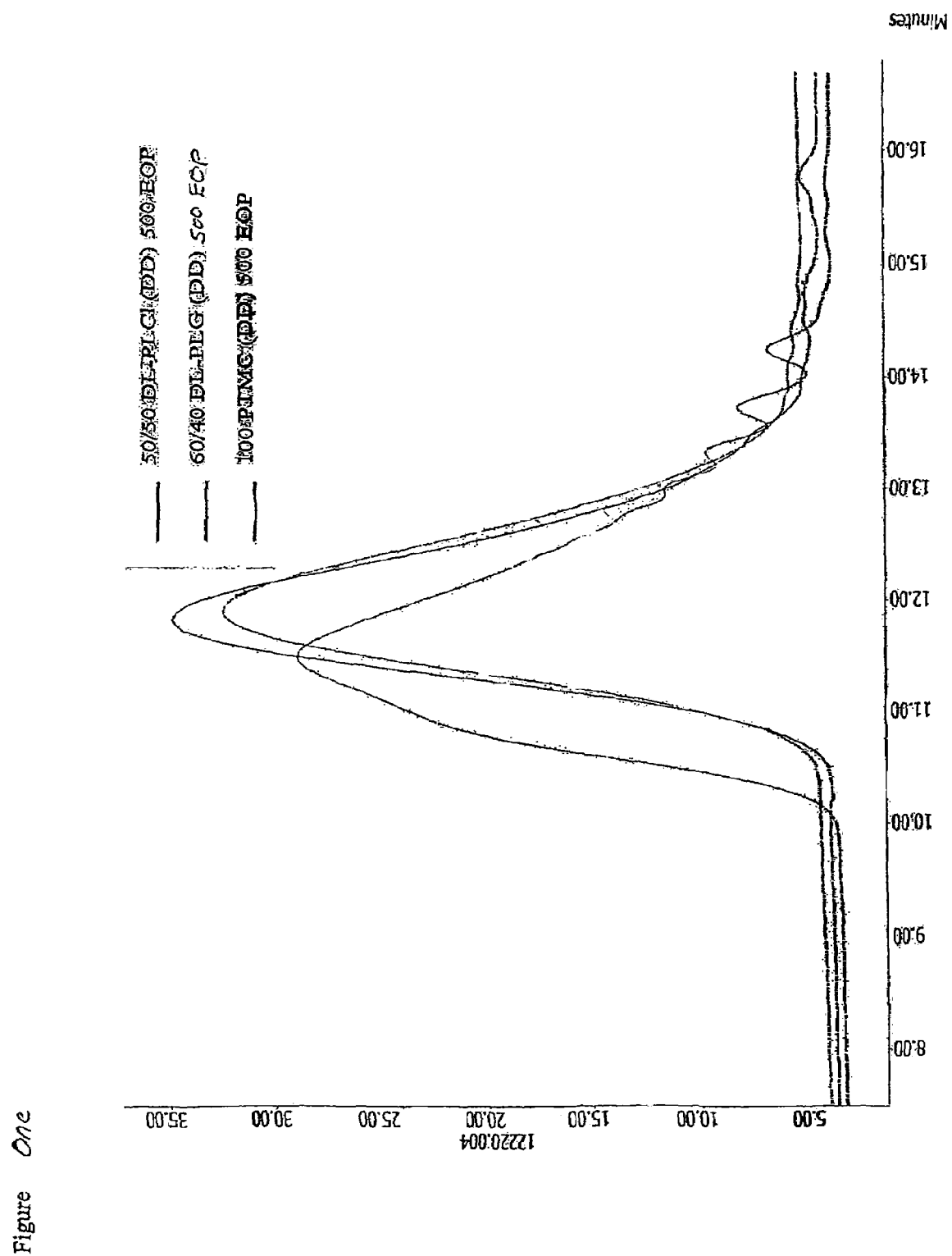
Figure One

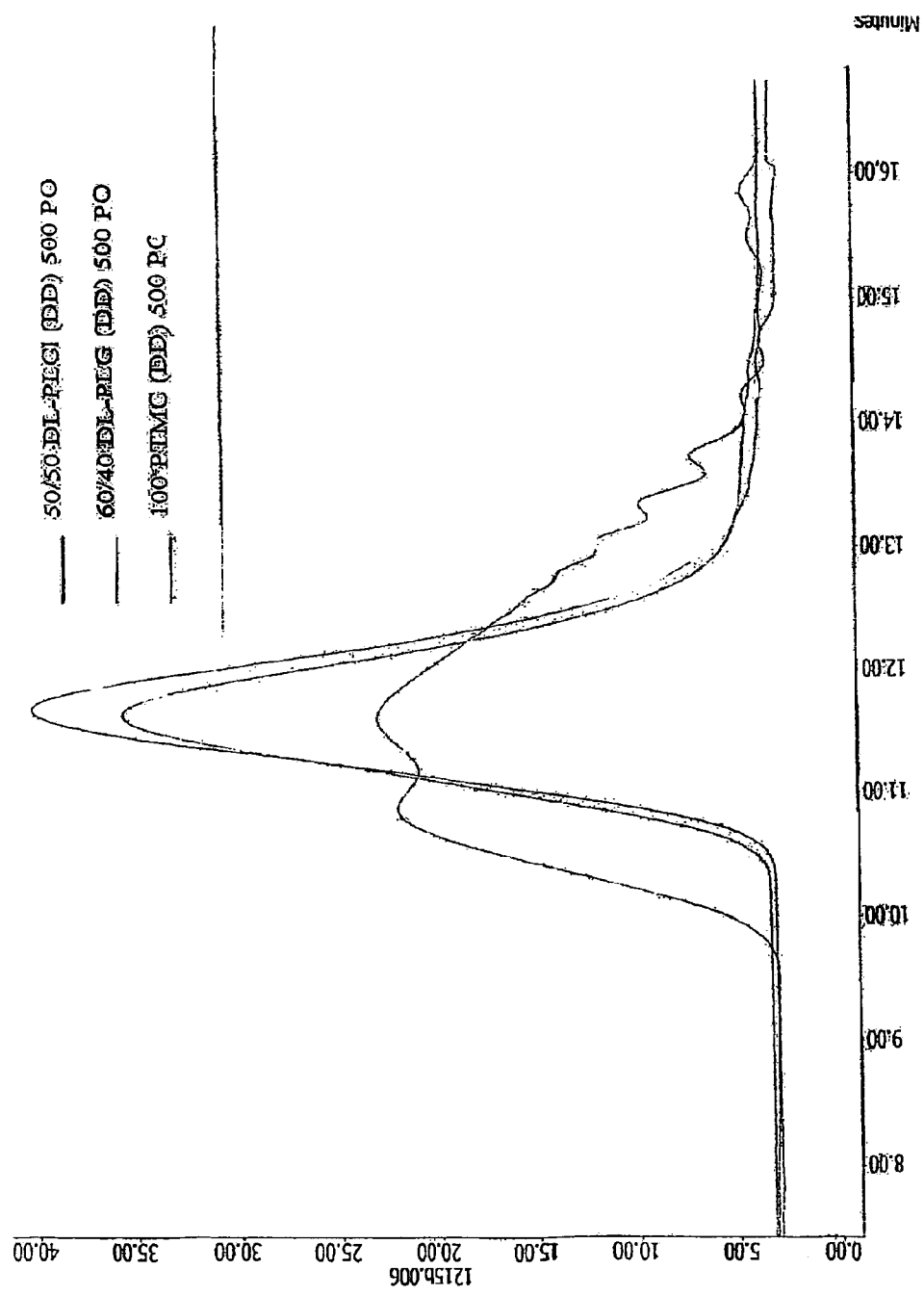
Figure Two

PHOSPHOROUS-CONTAINING COMPOUNDS WITH POLYMERIC CHAINS, AND METHODS OF MAKING AND USING THE SAME

RELATED APPLICATIONS

This application is a 35 U.S.C. 371 of PCT/US03/05795 filed Feb. 25, 2003, which claims priority to U.S. Ser. No. 60/359,314 filed Feb. 25, 2002, both of which are incorporated by reference in their entirety.

INTRODUCTION

A variety of approaches have been developed to permit the sustained release of drugs in a patient. These controlled release systems achieve a number of goals, including protecting the drug from the biological environment prior to delivery, and permitting the controlled release of the drug to a targeted area.

A number of conventional controlled release systems are based on solid microstructures, such as liposheres, liposomes, microcapsules, microparticles, and nanoparticles. The microstructures are typically introduced into the body of a subject in the form of a dispersion.

Conventional controlled delivery systems may also be prepared as solid macrostructures. An active agent, such as a drug, may be blended with a polymer. The blend may then be shaped into a specific form such as a cylinder, disc or fiber for implantation. The drug delivery system is then typically inserted into the body through an incision. These incisions are often larger than desired and may lead to a reluctance on the part of the subject to accept such a treatment. Additionally, a solid foreign body may produce irritation or discomfort in the patient, since the shape of the structure does not conform to the surrounding tissues.

A liquid composition for delivery of a therapeutic agent that remains liquid upon introduction into the body has a variety of potentially desirable features, including, for example: increasing patient comfort, providing for uniform release of the agent, and allowing for simple formulation and administration. Alternatively, a liquid composition that remains liquid prior to and during administration at room temperature and then becomes more viscous or even a solid at the in vivo temperature of a subject also has a variety of potentially desirable features, including, for example: allowing for easy administration, often by injection, of a liquid which behaves more like a solid in vivo. In part, the present invention is directed to certain phosphorus-containing compounds with two or more polymeric chains that may exhibit some or all of these features.

SUMMARY OF THE INVENTION

In part, the present invention is directed to phosphorus-containing compounds having two or three polymeric chains bound to a phosphorus atom, and methods of making and using the same. In another part, the present invention is directed to compositions comprising (i) a phosphorus-containing compound having two or three polymeric chains bound to a phosphorus atom, and (ii) a therapeutic agent, and methods of making and using the same.

In certain embodiments, the subject phosphorus-containing compounds have a phosphorus atom, such as, for example, phosphate, phosphonate or phosphite, with one, two or three polymeric chains, or chains, bound as substituents to the phosphorus atom. Such compounds may also be referred to as a "star polymer", in which there are two or three chains, or arms, that emanate from a central unit, in this case a phosphorus atom.

In general, such compounds may be represented as follows:

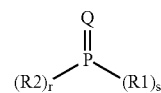

wherein: Q is a heteroatom, R1 is a polymeric chain, R2 is another chemical moiety, and r represents 0 or 1 and s represents 3 or 2, such that r+s=3.

In part, the present invention is directed towards such phosphorus-containing compounds and methods of making and using the same. In certain embodiments, the subject phosphorus-containing compounds may be biocompatible, biodegradable, or both. In certain embodiments, the subject phosphorus-containing compounds may be liquid. In certain embodiments, the subject phosphorus-containing compounds may be solid. In still other embodiments, the subject phosphorus-containing compounds may be amphiphilic. In still other embodiments, the subject phosphorus-containing compounds may have two polar regions and one non-polar region, or visa-versa. In yet other embodiments, the subject phosphorus-containing compounds may exhibit reverse thermal gelation.

The polymeric chains of the subject compounds may have any of the structures described below. The chemical structure of the polymeric chains may be varied to achieve a variety of desirable physical or chemical characteristics, including for example, release profiles or handling characteristics of the resulting subject compounds.

A number of therapeutic agents are contemplated for use with the present invention as described in more detail below.

In another aspect, the subject invention provides subject phosphorus-containing compounds exhibiting reverse thermal gelation behavior. In certain embodiments, such subject compounds may be used as a liquid drug delivery device, whereby a therapeutic agent is encapsulated in a gel formed by the liquid after administration to a patient. In certain embodiments, the agent is then released from the gel depot in a sustained fashion.

The subject phosphorus-containing compounds, and methods of making and using the same, achieve a number of desirable results and features, one or more of which (if any) may be present in any particular embodiment of the present invention: (i) a single dose of a subject composition may achieve a desired therapeutic affect through sustained release of a therapeutic agent encapsulated therein; (ii) sustained release of a therapeutic agent from a biocompatible and optionally biodegradable composition; (iii) novel treatment regimens for prevention or relief from a medical condition using the subject compositions; (iv) high levels of loading (by weight), e.g. greater than 10% and up to 50% or more, of a therapeutic agent in a biocompatible and optionally biodegradable composition; (v) a liquid composition for easy administration; (vi) co-encapsulation of other therapeutic agents in addition to any therapeutic agent; (vii) in certain embodiments, the subject phosphorus-containing compounds exhibit reverse thermal gelation behavior.

The present invention provides for methods of making the subject phosphorus-containing compounds and compositions containing them. In part, the subject invention is directed to preparations of formulations of subject phosphorus-containing compounds comprising a therapeutic agent.

In certain embodiments, subject compositions may be used a drug delivery device, such as a coating on a stent or catheter or as a solid medical device, and in certain embodiments, such subject compositions contain a therapeutic agent.

In another aspect, the subject phosphorus-containing compounds may be used in the manufacture of a medicament for any number of uses, including, for example, treating any disease or other treatable condition of a patient.

In another aspect, the present invention is directed to methods of using the subject phosphorus-containing compounds and compositions containing them for prophylactic or therapeutic treatment. In certain instances, the subject compositions may be used to prevent a disease or condition. In certain embodiments, use of the subject compositions that release a therapeutic agent in a sustained manner allows for different treatment regimens than are possible with other modes of administration of such therapeutic agents. In certain embodiments, administration of the subject polymers results in sustained release of an encapsulated therapeutic agent for a period of time and in an amount that is not possible with other modes of administration of the therapeutic agent. In another aspect of the invention, the efficacy of treatment using the subject compositions may be compared to treatment regimens known in the art in which a therapeutic agent is not encapsulated within a subject composition or other polymer for sustained release.

In other embodiments, this invention contemplates a kit including subject compositions, and optionally instructional material for their use. Uses for such kits include, for example, therapeutic applications.

These embodiments of the present invention, other embodiments, and their features and characteristics, will be apparent from the description, drawings and claims that follow.

BRIEF DESCRIPTION OF THE DRAWINGS

FIG. 1: Overlay of chromatograms for subject phosphorus-containing compounds with two polymeric chains.

FIG. 2: Overlay of chromatograms for subject phosphorus-containing compounds with three polymeric chains.

DETAILED DESCRIPTION OF THE INVENTION

A. Introduction

The present invention relates in part to compositions comprising phosphorus-containing compounds having two or more polymeric chains and a therapeutic agent, and methods of making and using the same. In certain embodiments, such compositions may be used to achieve sustained release of a therapeutic agent. In other embodiments, the present invention relates to the phosphorus-containing compounds themselves and methods of making and using the same. The present invention also relates to methods of administering such compositions for treatment of a subject. The dosage of the subject compositions may be adjusted as is necessary depending on the subject being treated, the severity of the affliction, the judgment of the prescribing physician, and the like.

B. Definitions

For convenience, before further description of the present invention, certain terms employed in the specification, examples, and appended claims are collected here. These definitions should be read in light of the remainder of the disclosure and understood as by a person of skill in the art. In particular, terms used herein that relate to polymers should be understood with reference to the definition of those terms by IUPAC as appropriate.

The articles "a" and "an" are used herein to refer to one or to more than one (i.e. to at least one) of the grammatical object of the article. By way of example, "an element" means one element or more than one element.

The term "access device" is an art-recognized term and includes any medical device adapted for gaining or maintaining access to an anatomic area. Such devices are familiar to artisans in the medical and surgical fields. An access device may be a needle, a catheter, a cannula, a trocar, a tubing, a shunt, a drain, or an endoscope such as an otoscope, nasopharyngoscope, bronchoscope, or any other endoscope adapted for use in the head and neck area, or any other medical device suitable for entering or remaining positioned within a preselected anatomic area.

The term "biocompatible plasticizer" is art-recognized, and refers to materials which are soluble or dispersible in the compositions of the present invention, which increase the flexibility of the composition, and which, in the amounts employed, are biocompatible. Suitable plasticizers are well known in the art and include those disclosed in U.S. Pat. Nos. 2,784,127 and 4,444,933. Specific plasticizers include, by way of example, acetyl tri-n-butyl citrate (c. 20 weight percent or less), acetyl trihexyl citrate (c. 20 weight percent or less), butyl benzyl phthalate, dibutyl phthalate, dioctylphthalate, n-butyryl tri-n-Hexyl citrate, diethylene glycol dibenzoate (c. 20 weight percent or less) and the like.

The terms "biocompatible composition" and "biocompatibility" when used in relation to a composition or molecule are art-recognized. For example, biocompatible materials include materials that are neither themselves toxic to the host (e.g., an animal or human), nor degrade (if the material degrades) at a rate that produces products at toxic concentrations in the host. It is not necessary that any subject composition have a purity of 100% to be deemed biocompatible; indeed, it is only necessary that the subject compositions be biocompatible as set forth above.

To determine whether material is biocompatible, it may be necessary to conduct a toxicity analysis. Such assays are well known in the art. One example of such an assay may be performed with live carcinoma cells, such as GT3TKB tumor cells, in the following manner: the sample is degraded in 1M NaOH at 37° C. until complete degradation is observed. The solution is then neutralized with 1M HCl. About 200 µL of various concentrations of the degraded sample products are placed in 96-well tissue culture plates and seeded with human gastric carcinoma cells (GT3TKB) at $10^4$/well density. The degraded sample products are incubated with the GT3TKB cells for 48 hours. The results of the assay may be plotted as % relative growth vs. concentration of degraded sample in the tissue-culture well. In addition, compositions of the present invention may also be evaluated by well-known in vivo tests, such as subcutaneous implantations in rats to confirm that they do not result in significant levels of irritation or inflammation at the subcutaneous implantation sites.

The term "biodegradable" is art-recognized, and refers to materials, such as certain of the subject phosphorus-containing compounds, that degrade during use. In general, degradation in vivo of certain of the subject phosphorus-containing compounds is believed to occur at least in part by hydrolysis of the phosphorus atom-substituent bond, and also possibly by hydrolysis of the subunits of any polymeric chain. The degradation rate of a biodegradable subject compound in vivo often depends in part on a variety of factors, including the chemical identity of the linkage responsible for any degradation, the molecular weight, viscosity, biostability, and degree of cross-linking of such compound, and the mode and location of administration.

The term "delivery agent" is an art-recognized term, and refers to molecules that facilitate the intracellular delivery of a therapeutic agent or other material. Examples of delivery agents include: sterols (e.g., cholesterol) and lipids (e.g., a cationic lipid, virosome or liposome).

"Drug delivery device" is an art-recognized term and refers to any medical device suitable for the application of a therapeutic agent to a targeted organ or anatomic region. The term includes, without limitation, those subject compositions containing a subject-phosphorus compound and a therapeutic agent that releases the therapeutic agent into the surrounding tissues of an anatomic area. The term further includes those devices that transport or accomplish the instillation of the subject compositions towards the targeted organ or anatomic area, even if the device itself is not formulated to include the composition. As an example, a needle or a catheter through which the composition is inserted into an anatomic area or into a blood vessel or other structure related to the anatomic area is understood to be a drug delivery device. As a further example, a stent or a shunt or a catheter that has a subject composition included in its substance or coated on its surface is understood to be a drug delivery device.

"Drug delivery liquid exhibiting reverse thermal gelation" means a solution or mixture that contains a subject phosphorus-containing compound exhibiting reverse thermal gelation and a therapeutic agent (the agent may or may not be fully dissolved in the solution) suitable for administration to a patient, whereupon if the thermal gelation temperature of the liquid is below the body temperature of the patient, the liquid forms a gelled depot.

The term "$ED_{50}$" is art-recognized and refers to the dose of a drug that produces 50% of its maximum response or effect, or alternatively, the dose that produces a pre-determined response in 50% of test subjects. The term "$LD_{50}$" is art-recognized, and refers to the dose of a drug which is lethal in 50% of test subjects. The term "therapeutic index" is an art-recognized term that refers to the therapeutic index of a drug, defined as $LD_{50}/ED_{50}$.

The term "fluid" is art-recognized and refers to a non-solid state of matter in which the atoms or molecules are free to move in relation to each other, as in a gas or liquid. If unconstrained upon application, a fluid material may flow to assume the shape of the space available to it, covering for example, the surfaces of an excisional site or the dead space left under a flap. A fluid material may be inserted or injected into a limited portion of a space and then may flow to enter a larger portion of the space or its entirety. Such a material may be termed "flowable." This term includes, for example, liquid compositions that are capable of being sprayed into a site; injected with a manually operated syringe fitted with, for example, a 23-gauge needle; or delivered through a catheter. Also included in the term "flowable" are those highly viscous, "gel-like" materials at room temperature that may be delivered to the desired site by pouring, squeezing from a tube, or being injected with any one of the commercially available injection devices that provide injection pressures sufficient to propel highly viscous materials through a delivery system such as a needle or a catheter. In certain instances, flowable subject compositions have the ability to assume, over time, the shape of the space containing it at body temperature.

The term "gel" means a semi-solid phase of a mixture or material. In certain instances, a gel spontaneously occurs as the temperature of a solution of a subject phosphorus-containing compound exhibiting reverse thermal gelation or a drug delivery liquid exhibiting reverse thermal gelation is raised to or above the gelation temperature of the compound or liquid.

The term "gelation temperature" is art-recognized and means as used herein the temperature at which a subject phosphorus-containing compound, or a mixture containing such a compound, undergoes reverse thermal gelation, i.e. the temperature below which the compound is soluble in a solvent (e.g., water) and above which the compound undergoes phase transition to increase in viscosity or to form a semi-solid gel in the same solvent. It is understood that the gelation temperature for a mixture may differ from the temperature observed for a subject phosphorus-containing compound contained in the mixture. The terms "gelation temperature" and "reverse thermal gelation temperature" or the like shall be used interchangeably in referring to the gelation temperature.

The term "gelled depot" means the gel formed by a drug delivery liquid exhibiting reverse thermal gelation following administration to a patient whose body temperature is above the gelation temperature of the liquid.

The terms "incorporated" or "encapsulate" are art-recognized and refer to formulating or otherwise including a therapeutic agent into a composition of the present invention containing a subject phosphorus-containing compound. The terms "co-incorporation" or "co-encapsulation" are art-recognized and refer to the incorporation of a therapeutic agent or other material and at least one other therapeutic agent or other material in a subject composition.

The term "instructional material" or "instructions" includes a publication, a recording, a diagram, or any other medium of expression which can be used to communicate the usefulness of a subject composition described herein for a method of treatment or a method of making or using a subject composition. The instructional material may, for example, be affixed to a container which contains the composition or be shipped together with a container which contains the composition or be contained in a kit with the composition. Alternatively, the instructional material may be shipped separately from the container with the intention that the instructional material and the composition be used cooperatively by the recipient.

The terms "number average molecular weight", or "Mn", "weight average molecular weight", "Z-average molecular weight" and "viscosity average molecular weight" are art-recognized. When the term "molecular weight" or an exemplary molecular weight is described herein, the measure of molecular weight will be clear from the context and/or will include all applicable measures.

The phrases "parenteral administration" and "administered parenterally" are art-recognized terms, and refer to modes of administration other than enteral and topical administration, such as injections, and include, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

A "patient," "subject," or "host" to be treated by a subject method refers to either a human or non-human animal, such as primates, mammals, and vertebrates.

The phrase "pharmaceutically acceptable" is art-recognized and refers to subject compositions and other materials and/or dosage forms which are, within the scope of sound medical judgment, suitable for use in contact with the tissues of patients without excessive toxicity, irritation, allergic response, or other problem or complication, commensurate with a reasonable benefit/risk ratio.

The phrase "pharmaceutically acceptable carrier" is art-recognized, and refers to, for example, pharmaceutically acceptable materials, compositions or vehicles, such as a liquid or solid filler, diluent, excipient, solvent or encapsulating material, involved in carrying or transporting any administered composition from one organ, or portion of the body, to another organ, or portion of the body. Each carrier must be "acceptable" in the sense of being compatible with the other ingredients of such composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" is art-recognized, and refers to relatively non-toxic, inorganic and organic acid addition salts of molecules, such as therapeutic agents. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, *J. Pharm. Sci.* 66:1-19 (1977).

The term "prophylactic" or "therapeutic" treatment is art-recognized and refers to administration to the host of one or more of the subject compositions. If it is administered prior to clinical manifestation of the unwanted condition (e.g., disease or other unwanted state of the host animal), then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The term "preventing", when used in relation to a condition, such as cancer, an infectious disease or other medical condition, is art-recognized, and refers to administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population.

The term "random" is art-recognized and is intended to refer to the situation in which the particular distribution or incorporation of monomeric units in a polymer or polymeric chain that has more than one type of unit is not directed or controlled directly by the synthetic protocol, but instead results from features inherent to the polymer or polymeric chain, such as the reactivity, amounts of subunits and other characteristics of the synthetic reaction or other methods of manufacture, processing or treatment.

The phrase "reverse thermal gelation" is an art-recognized term and refers to the phenomena whereby a solution of a molecule, here a subject phosphorus-containing compound, spontaneously increases in viscosity, and in many instances transforms into a semisolid gel, as the temperature of the solution is increased above the gelation temperature of the molecule. In many instances, the solvent is polar in character, and is often water. For the purposes of the invention, the term "gel" includes both the semisolid gel state and the high viscosity state that exists above the gelation temperature for any molecule. When cooled below the gelation temperature, the gel spontaneously reverses to reform the lower viscosity solution. Ideally, this cycling between the solution and the gel may be repeated ad infinitum because the sol/gel transition does not involve any change in the chemical composition of the polymer system, for all interactions to create the gel are physical in nature and do not involve the formation or breaking of covalent bonds in the molecule. Such behavior may be observed and quantified by a number of methods known in the art.

"Small molecule" is an art-recognized term, and refers to a molecule which has a molecular weight of less than about 2000 amu, or less than about 1000 amu, and even less than about 500 amu.

When used with respect to a therapeutic agent or other material, the term "sustained release" is art-recognized. For example, a composition which releases a substance over time may exhibit sustained release characteristics, in contrast to a bolus type administration in which the entire amount of the substance is made biologically available at one time. In particular embodiments, upon contact with body fluids after administration, a subject composition comprising a phosphorus-containing compound and a therapeutic agent may release the therapeutic agent for a sustained or extended period (as compared to the release from a bolus). This release may result in prolonged delivery of therapeutically effective amounts of such incorporated therapeutic agent.

The phrases "systemic administration," "administered systemically," "peripheral administration" and "administered peripherally" are art-recognized, and refer to the administration of a composition or other material other than directly into the central nervous system, e.g., by subcutaneous administration, such that it enters the patient's system and, thus, is subject to metabolism and other like processes.

The phrase "therapeutically effective amount" is an art-recognized term, and refers to an amount of a therapeutic agent that produces some desired effect at a reasonable benefit/risk ratio applicable to any medical treatment. In those embodiments in which the composition administered comprises a phosphorus-containing compound and a therapeutic agent, the therapeutically effective amount of the composition (as opposed to the therapeutic agent itself) will vary with the nature of the phosphorus-containing compound, the loading level of the therapeutic agent in the composition, the mode and method of administration, whether any other materials are incorporated in the composition, the disease or condition being treated, the size of the subject, the severity of the disease or condition, and other factors known to one of skill in the art. One of skill in the art may empirically determine the effective amount of a particular compound without necessitating undue experimentation.

The term "treating" is an art-recognized term which refers to curing as well as ameliorating at least one symptom of any condition or disease.

"Viscosity" is an art-recognized term, and in this context refers to the resistance to flow exhibited by a liquid. "Absolute viscosity" is an art-recognized term, and refers to viscosity measured by sensing the torque required to rotate a spindle at constant speed while immersed in the sample fluid. The torque is proportional to the viscous drag on the immersed spindle, and thus to the viscosity of the fluid.

For purposes of this invention, the chemical elements are identified in accordance with the Periodic Table of the Elements, CAS version, Handbook of Chemistry and Physics, 67th Ed., 1986-87, inside cover.

The term "acylamino" is art-recognized and refers to a moiety that may be represented by the general formula:

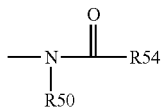

wherein R50 is as defined above, and R54 represents a hydrogen, an alkyl, an alkenyl or —(CH$_2$)$_m$—R61, where m and R61 are as defined above.

The term "aliphatic" is an art-recognized term and refers to linear, branched, and cyclic alkanes, alkenes, or alkynes. In certain embodiments, aliphatic groups in the present invention are linear or branched and have from 1 to about 20 carbon atoms.

The terms "alkenyl" and "alkynyl" are art-recognized, and refer to unsaturated aliphatic groups analogous in length and possible substitution to the alkyls described above, but that contain at least one double or triple bond respectively.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., C$_1$-C$_{30}$ for straight chain, C$_3$-C$_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" is also defined to include halosubstituted alkyls.

Moreover, the term "alkyl" (or "lower alkyl") includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN and the like. Exemplary substituted alkyls are described below. Cycloalkyls may be further substituted with alkyls, alkenyls, alkoxys, alkylthios, aminoalkyls, carbonyl-substituted alkyls, —CN, and the like.

Unless the number of carbons is otherwise specified, "lower alkyl" refers to an alkyl group, as defined above, but having from one to ten carbons, alternatively from one to about six carbon atoms in its backbone structure. Likewise, "lower alkenyl" and "lower alkynyl" have similar chain lengths.

The term "alkylthio" is art-recognized and refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "amido" is art-recognized as an amino-substituted carbonyl and refers to a moiety that may be represented by the general formula:

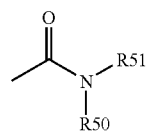

wherein R50 and R51 are as defined above. Certain embodiments of the amide in the present invention will not include imides which may be unstable.

The terms "amine" and "amino" are art-recognized and refers to both unsubstituted and substituted amines, e.g., a moiety that may be represented by the general formulas:

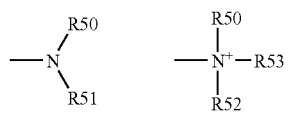

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "aralkyl" is art-recognized, and refers to alkyl groups substituted with an aryl group (e.g., an aromatic or heteroaromatic group).

The term "aryl" is art-recognized, and refers to 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The term "carbocycle" is art-recognized and refers to an aromatic or non-aromatic ring in which each atom of the ring is carbon. The flowing art-recognized terms have the following meanings: "nitro" means —NO$_2$; the term "halogen" designates —F, —Cl, —Br or —I; the term "sulfhydryl" means —SH; the term "hydroxyl" means —OH; and the term "sulfonyl" means —SO$_2^-$.

The term "carbonyl" is art-recognized and refers to such moieties as may be represented by the general formulas:

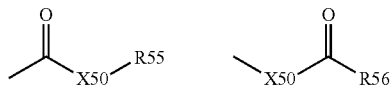

wherein X50 is a bond or represents an oxygen or a sulfur, and R55 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiocarbonyl" group. Where X50 is a sulfur and R55 or R56 is not hydrogen, the formula represents a "thioester." Where X50 is a sulfur and R55 is hydrogen, the formula represents a "thiocarboxylic acid." Where X50 is a sulfur and R56 is hydrogen, the formula represents a "thioformate." On the other hand, where X50 is a bond, and R55 is not hydrogen, the above formula represents a "ketone" group. Where X50 is a bond, and R55 is hydrogen, the above formula represents an "aldehyde" group.

The term "electron-withdrawing group" is art-recognized, and refers to the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, March, *Advanced Organic Chemistry* 251-59, McGraw Hill Book Company, New York, (1977). The Hammett constant values are generally negative for electron donating groups (σ(P)=–0.66 for NH$_2$) and positive for electron withdrawing groups (σ(P)=0.78 for a nitro group), σ(P) indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "heteroatom" is art-recognized, and refers to an atom of any element other than carbon or hydrogen. Illustrative heteroatoms include boron, nitrogen, oxygen, phosphorus, sulfur and selenium, and alternatively oxygen, nitrogen or sulfur.

The terms "heterocyclyl" and "heterocyclic group" are art-recognized, and refer to 3- to about 10-membered ring structures, such as 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "hydrocarbon" is art-recognized and refers to all permissible compounds having at least one hydrogen and one carbon atom. For example, permissible hydrocarbons include acyclic and cyclic, branched and unbranched, carbocyclic and heterocyclic, aromatic and nonaromatic organic compounds that may be substituted or unsubstituted.

The phrase "hydroxyl-protecting group" is art-recognized and refers to those groups intended to protect a hydroxyl group against undesirable reactions during synthetic procedures and includes, for example, benzyl or other suitable esters or ethers groups known in the art.

The abbreviations Me, Et, Ph, Tf, Nf, Ts, and Ms are art-recognized and refer to methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The term "phosphoramidite" is art-recognized and refers to moieties represented by the general formulas:

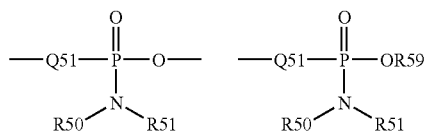

wherein Q51, R50, R51 and R59 are as defined above.

The term "phosphonamidite" is art-recognized and refers to moieties represented by the general formulas:

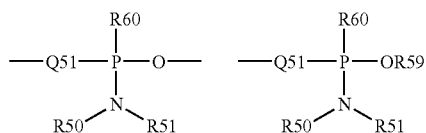

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The terms "polycyclyl" and "polycyclic group" are art-recognized, and refer to structures with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms, e.g., three or more atoms are common to both rings, are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The phrase "protecting group" is art-recognized and refers to temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed. Greene et al., *Protective Groups in Organic Synthesis* 2$^{nd}$ ed., Wiley, New York, (1991).

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—(CH$_2$)$_m$—R61, m and R61 being defined above.

The term "substituted" is art-recognized and refers to all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "sulfate" is art-recognized and refers to a moiety that may be represented by the general formula:

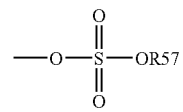

in which R57 is as defined above.

The term "sulfonate" is art-recognized and refers to a moiety that may be represented by the general formula:

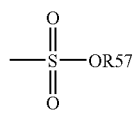

in which R57 is an electron pair, hydrogen, alkyl, cycloalkyl, or aryl.

The term "sulfonamido" is art-recognized and refers to a moiety that may be represented by the general formula:

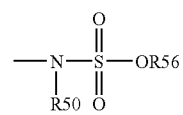

in which R50 and R56 are as defined above.

The term "sulfamoyl" is art-recognized and refers to a moiety that may be represented by the general formula:

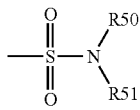

in which R50 and R51 are as defined above.

The term "sulfonyl" is art-recognized and refers to a moiety that may be represented by the general formula:

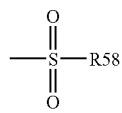

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

in which R58 is defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The definition of each expression, e.g. alkyl, m, n, etc., when it occurs more than once in any structure, is intended to be independent of its definition elsewhere in the same structure unless otherwise indicated expressly or by the context.

Contemplated equivalents of the subject compounds and compositions described herein include such materials which otherwise correspond thereto, and which have the same general properties thereof (e.g., biocompatible), wherein one or more simple variations of substituents are made which do not adversely affect the efficacy of such molecule to achieve its intended purpose. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

C. Subject Phosphorus-Containing Compounds

Phosphorus-containing compounds are in part the subject of the present invention. In certain embodiments, the subject phosphorus-containing compounds have a phosphorus atom with two or three polymeric chains, or chains, as substituents to the phosphorus atom. Such compounds may also be referred to as a "star polymer", in which there are two or three chains, or arms, that emanate from a central unit, in this case a phosphorus atom (with additional appropriate substituents to the central phosphorus atom to complete its valency).

Exemplary phosphorus atoms that may serve as the central unit in subject compounds include, without limitation, phosphonamidite, phosphoramidite, phosphorodiamidate, phosphomonoester, phosphodiester, phosphotriester, phosphonate, phosphonate ester, phosphorothioate, thiophosphate ester, phosphinate or phosphite.

The subject phosphorus-containing compounds may be biodegradable, biocompatible or both.

A formulaic representation of certain embodiments of the present invention is:

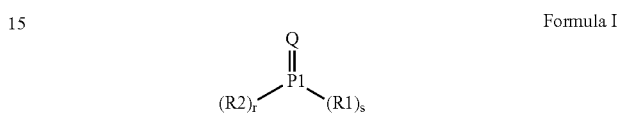

Formula I wherein:
Q represents —O or —N(R3);
r represents 0 or 1, and s represents 3 or 2, such that r+s=3;
R1 represents a polymeric chain;
R2 is described below and is not equal to R1; and
R3 represents —H, alkyl, aryl, cycloalkyl, cycloalkenyl, heterocycle or polycycle.

R2 may be any chemical moiety as long as it does not materially interfere with the synthesis or biocompatibility (or both) of the subject phosphorus-containing compound in question, wherein a "material interference" is understood to mean: (i) for synthesis of such phosphorus-containing compound, an inability to prepare such compound by methods known in the art or taught herein, and (ii) for biocompatibility, a reduction in the biocompatibility of such compound so as to make such compound impracticable for in vivo use.

In certain embodiments, R2 may be a polymeric chain different from R1. Exemplary R2 are any R1 described below or any other polymeric chains including: poly(ethylene glycol), poly(vinyl alcohols), pluronics (e.g., poly(ethylene glycol)-co-(polypropylene glycol) or poly(ethylene glycol)-block-(polypropylene glycol) commercially available from BASF), polyamides, polycarbonates, polyalkylenes, polyacrylamides, polyanhydrides, poly(phosphoesters), polyalkylene glycols, polyalkylene oxides, polyalkylene terephthalates, polyvinyl ethers, polyvinyl esters, polyvinyl halides, polyvinylpyrrolidone (PVP), polyglycolides, polysiloxanes, polyphosphates and polyurethanes, alkyl celluloses, hydroxyalkyl celluloses, cellulose ethers, cellulose esters, and nitrocelluloses.

In certain embodiments, R2 is —H, alkyl, cycloakyl, —O-alkyl, —O-cycloalkyl, cycloalkenyl, —O-cycloalkenyl, aryl, —O-aryl, heterocycle, —O-Heterocycle, polycycle, —O-polycycle, or —N(R4)R5, wherein R4 and R5, each independently, represent a hydrogen, an alkyl, an alkenyl, —(CH2)m-R6, or R4 and R5, taken together with the N atom to which they are attached complete a heterocycle having from 4 to about 8 atoms in the ring structure; m represents an integer from 0-10; and R6 represents —H, alkyl, cycloakyl, —O-alkyl, —O-cycloalkyl, cycloalkenyl, —O-cycloalkenyl, aryl, —O-aryl, heterocycle, —O-heterocycle, polycycle, —O-polycycle.

Possible alkyl R2 groups include methyl, ethyl, n-propyl, i-propyl, n-butyl, tert-butyl, —$C_8H_{17}$ and the like groups; and alkyl substituted with a non-interfering substituent, such as hydroxy, halogen, alkoxy or nitro; corresponding alkoxy groups.

In certain embodiments, when R2 is aryl or the corresponding aryloxy group, it typically contains from about 5 to about 14 carbon atoms, or about 5 to about 12 carbon atoms, and optionally, may contain one or more rings that are fused to each other. Examples of particularly suitable aromatic groups include phenyl, phenoxy, naphthyl, anthracenyl, phenanthrenyl and the like.

In certain embodiments, when R2 is a heterocycle, it typically contains from about 5 to about 14 ring atoms, alternatively from about 5 to about 12 ring atoms, and one or more heteroatoms. Examples of suitable heterocyclic groups include furan, thiophene, pyrrole, isopyrrole, 3-isopyrrole, pyrazole, 2-isoimidazole, 1,2,3-triazole, 1,2,4triazole, oxazole, thiazole, isothiazole, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-dioxazole, 1,2,4-dioxazole, 1,3,2-dioxazole, 1,3,4-dioxazole, 1,2,5-oxatriazole, 1,2-pyran, 1,4-pyran, 1,2-pyrone, 1,4-pyrone, 1,2-dioxin, 1,3-dioxin, pyridine, N-alkyl pyridinium, pyridazine, pyrimidine, pyrazine, 1,3,5-triazine, 1,2,4-triazine, 1,2,3-triazine, 1,2-oxazine, 1,3-oxazine, 1,4-oxazine, o-isoxazine, p-isoxazine, 1,2,5-oxathiazine, 1,2,6-oxathiazine, 1,4,2-oxadiazine, 1,3,5-oxadiazine, azepine, oxepin, thiepin, indene, isoindene, benzofuran, isobenzofuran, thionaphthene, isothionaphthene, indole, indolenine, 2-isobenzazole, isoindazole, indoxazine, benzoxazole, anthranil, 1,2-benzopyran, 1,2-benzopyrone, 1,4-benzopyrone, 2,1-benzopyrone, 2,3-benzopyrone, quinoline, isoquinoline, 12, -benzodiazine, 1,3-benzodiazine, naphthyridine, pyrido-[3,4-b]-pyridine, pyrido-[3,2-b]-pyridine, pyrido-[4,3-b]-pyridine, 1,3,2-benzoxazine, 1,4,2-benzoxazine, 2,3,1-benzoxazine, 3,1,4-benzoxazine, 1,2-benzisoxazine, 1,4-benzisoxazine, carbazole, xanthrene, acridine, purine, and the like. In certain embodiments, R2 is selected from the group consisting of furan, pyridine, N-alkylpyridine, 1,2,3- and 1,2,4-triazoles, indene, anthracene and purine rings.

In certain embodiments, R2 is an alkyl group, an alkoxy group, a phenyl group, a phenoxy group, a heterocycloxy group, or an ethoxy group.

R1 is a polymeric chain. The term "polymeric chain" or "chain" is art-recognized, and refers to a chemical moiety comprising a sequence of constitutional units, or repeating units, between two repeating units that are boundary units. In the present invention, in certain embodiments, one of those boundary units is bound to the central phosphorus atom. The polymeric chains contemplated for the subject phosphorus-containing compounds include any polymeric chains that do not materially interfere with the synthesis or biocompatibility (or both) of the subject phosphorus-containing compound in question. In another aspect, the polymeric chain may comprise more than one type of repeating unit, or other portions that are not polymeric in nature, provided that the polymeric chain comprise at least one region that is polymeric in nature.

For purposes of the present invention, the constitutional unit of any polymeric chain contained in a subject phosphorus-containing compound does not include the central phosphorus atom to which the polymeric chains are attached. This means that the central phosphorus atom of the star polymer compound that are in part the inventive subject matter would not be considered by one of ordinary skill in the art to be part of the polymeric branches attached to such atom. Alternatively, this concept may be illustrated for Formula I above by the following: constitutional units of a polymeric chain in the subject phosphorus-containing compounds are other than

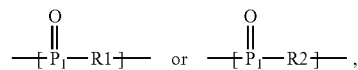

so that there is a phosphorus atom having the identity P1 above that is not part of a constitutional unit. Accordingly, the subject phosphorus-containing compounds are not a linear single-stranded macromolecule with the same constitutional or repeating units with a branch point in multiple repeating units at the central phosphorus atom P1. For example, the subject phosphorus-containing compounds do not include the polymers DNA or RNA, because there is no phosphorus atom that is not part of the repeating units of the DNA or RNA.

In certain embodiments, the repeating units in any one polymeric chain are the same, or are regular constitutional units (not taking into account any chirality contained in the repeating unit, which may be the same or may be different).

In certain embodiments, a polymeric chain may consist of only the boundary units, so that there are only two repeating units in the chain.

In certain embodiments, the polymeric chains are selected so that the resulting phosphorus-containing compound is flowable at room temperature.

In certain embodiments, the two or three polymeric chains attached to the central phosphorus atom have the same repeating unit, although it would usually be the case that the number of such units will vary in each chain. Such variance will usually result from the manner in which the molecule that is reacted to form the polymer chain is prepared, often by polymerization of monomers. Stated another way, the polymeric chains in a subject phosphorus-containing compounds may all consist of the same constitutional unit, although the number of constitutional units will likely vary.

In certain embodiments, the three polymeric chains attached to the central phosphorus atom will all have different repeating units, so that the three polymeric chains will be understood to be different from one another. This possibility would be the case in Formula I when s is equal to three and all three polymeric chains R2 are different from one another, e.g., have different constitutional units.

In certain embodiments, the polymeric chain R1 includes one or more portions of repreating units, as described above, plus other portions that are polymeric or not polymeric in nature. This result is depicted in one embodiment in Formula II below, where R7 is not part of the polymeric portion that gives rise to designation of the chemical moiety in Formula II as a polymeric branch.

In certain embodiments, R1 (when presented as a stable chemical moiety, such as prior to reaction with the central phosphorus atom) may itself be biodegradable.

The molecular weights of the R1 polymeric chains used in a subject phosphorus-containing compound may vary widely. In certain embodiments, the R1 polymeric chains of the subject compositions have molecular weights that may vary widely, but typically range ranging from about 250 up to about 100,000 daltons, or alternatively from about 300, 400, 500, 700, 800, 900 1,000, 1,500, 2,000, 2,500, 3,000, 4,000, 5,000, 10,000, 15,000, 20,000, 25,000, 30,000, 40,000, 50,000, 60,000, 70,000, 80,000, 90,000 and 100,000 daltons. Number-average molecular weight (Mn) for the polymeric chains may also vary widely, but generally fall in the range described above. The viscosity or flowability of the subject phosphorus-containing compounds will vary with the identity of the R1 polymeric chains. In general, either a larger molecular weight for a polymeric chain will result in higher viscosity (e.g. lower fluidity), whereas a lower molecular weight for a polymer chain will generally exhibit low viscosity.

In certain embodiments, the polymeric chain may contain phosphorus atoms.

In certain embodiments, R1 may be selected from any of the following general structures (Formulas IIa-f). In those formulas and others contained herein, "*" represents the central phosphorus atom P1.

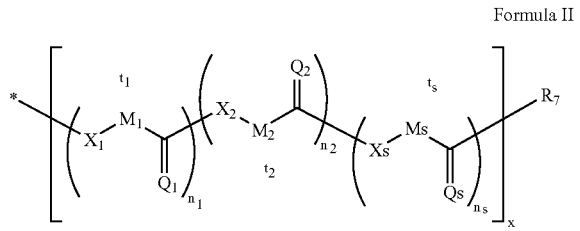

Formula II wherein,

R7 is defined below;

Q1, Q2 . . . Qs, each independently, represent —O or —N(R3);

X1, X2 . . . Xs, each independently, represent —O— or —N(R3)—;

the s of $t_s$ is an integer and at least 1 or more;

$n_1, n_2 \ldots n_s$ is greater than 0 to about 1000 or more;

x is an integer from 1 to about 1000 or more;

M1, M2 . . . Ms each independently are defined below; and all other moieties are defined above.

In Formula II, $t_s$ identifies a chemical moiety, with each such chemical moiety identified with a $t_s$ being a constitutional unit (or repeating unit) of the polymeric chain represented by Formula II. The number of times that each such unit $t_s$ appears in the unit x is represented by $n_s$, which may be a non-integer. In certain instances, $n_s$ may be an average of the number of times that any unit $t_s$ is present in the unit x for all the polymeric chains represented by Formula II in the subject phosphorus-containing compound, with x being equal to 1. Usually, the average is theoretically determined from the molar ratio of the starting materials that were used to make the polymeric chain precursor prior to the precursor being reacted with a phosphorus-containing reactant to provide the subject phosphorus-containing compound.

By this Formula II, polymeric chains having a complicated structure may be depicted. For example, a random order of ten different types of constitutional units in a polymeric chain may be depicted by Formula II, wherein each constitutional unit in the polymeric chain is assigned a new identifier t, and n, and x are both equal to 1. Alternatively, each different type of constitutional unit may be assigned a unique identifier $t_s$, with $n_s$ indicating the average number of times that each unique such type of unit is present in all the polymeric chains in the subject phosphorus-containing compound, with x being equal to 1.

In certain instances, all of the constitutional units are the same, whereupon s of Formula II is equal to one and there is one $t_s$ unit (which is the constitutional unit), and the number of constitutional units in the polymeric chain is equal to the product of $n_s$ times x. It may be the case that $n_s$ and x in such an instance is an average over all the polymeric chains represented by Formula II in the subject phosphorus-containing compound.

In Formula II, R7 is attached to the boundary constitutional unit of the polymeric chain represented by Formula II. In general, R7 may be any chemical moiety defined for R2 above, including any polymeric chain (other than the polymeric chain R1 bound to R7). In certain embodiments, R7 represents —O-alkyl, —O-cycloalkyl, —O-aryl, —O-heterocyclyl, —S-alkyl, —S-cycloalkyl, —S-aryl, —S-heterocyclyl, or —N(R4)R5. As described in general terms above, in certain embodiments R7 itself may be polymeric in nature, or may comprise one or more polymeric regions separated by non-polymeric regions. Although not depicted in Formula II, the present invention also contemplates that the polymeric region of that gives rise to the designation of the chemical moiety as a polymeric branch may not be directly bound to the central phosphorus atom, but may be bound to the central phosphorus atoms by one or more non-polymeric or polymeric regions.

M1, M2 . . . Ms (collectively, M) in Formula II may be each independently any chemical moiety that does not materially interfere with the synthesis or biocompatibility (or both) of the subject phosphorus-containing-compound in question.

For certain embodiments, M in the formula are each independently: (i) a branched or straight chain aliphatic or aryl group having from 1 to about 50 carbon atoms, (ii) a branched or straight chain, oxa-, thia-, or aza-aliphatic group having from 1 to about 50 carbon atoms, both optionally substituted; (iii) a branched or straight chain carboxlyalkyl group having from 1 to about 50 carbon atoms; or (iv) a branched or straight-chain alkoxycarbonyl-substituted alkyl group having from 1 to about 50 carbon atoms. In certain embodiments, the number of such carbon atoms does not exceed 20.

M may include an aromatic or heteroaromatic moiety, optionally with non-interfering substituents. In certain of those embodiments, none of the atoms (usually but not always C) that form the cyclic ring that gives rise to the aromatic moiety are part of the polymer chain backbone.

Specifically, when M is a branched or straight chain aliphatic group having from 1 to about 20 carbon atoms, it may be, for example, an alkylene group such as methylene, ethylene, 1-methylethylene, 1,2-dimethylethylene, n-propylene, trimethylene, isopropylene, 2,2-dimethylpropylene, n-pentylene, n-hexylene, n-heptylene, n-octylene, n-nonylene, n-decylene, n-undecylene, n-dodecylene, and the like; an alkenylene group such as n-propenylene, 2-vinylpropylene, n-butenylene, 3-hexylbutylene, n-pentenylene, 4-(3-propenyl)hexylene, n-octenylene, 1-(4-butenyl)-3-methyldecylene, 2-(3-propenyl)dodecylene, hexadecenylene and the like; an alkynylene group, such as ethynylene, propynylene, 3-(2ethynyl)pentylene, n-hexynylene, 2-(2-propynyl)decylene, and the like; or any alkylene, alkenylene or alkynylene group, including those listed above, substituted with a materially non-interfering substituent, for example, a hydroxy, halogen or nitrogen group, such as 2-chloro-n-decylene, 1-hydroxy-3-ethenylbutylene, 2-propyl-6-nitro-10-dodecynylene, and the like. Other M of the present invention include —$(CH_2)_3$—, —$(CH_2)_5$— and —$(CH_2)_2OCH_2$—.

When M is a branched or straight chain oxaaliphatic group having from 1 to about 20 carbon atoms, it may be, for example, a divalent alkoxylene group, such as ethoxylene, 2-methylethoxylene, propoxylene, butoxylene, pentoxylene, dodecyloxylene, hexadecyloxylene, and the like. When M is a branched or straight chain oxaaliphatic group, it may have the formula —$(CH_2)_a$—O—$(CH_2)_b$— wherein each of a and b, independently, is about 1 to about 7.

When M is a branched or straight chain oxaaliphatic group having from 1 to about 20 carbon atoms, it may also be, for example, a dioxaalkylene group such as dioxymethylene, dioxyethylene, 1,3-dioxypropylene, 2-methoxy-1,3-dioxypropylene, 1,3-dioxy-2-methylpropylene, dioxy-n-pentylene, dioxy-n-octadecylene, methoxylene-methoxylene, ethoxylene-methoxylene, ethoxylene-ethoxylene, methoxylene-1-propoxylene, butoxylene-n-propoxylene, pentadecyloxylene-methoxylene, and the like. When M is a branched or straight chain, dioxyaliphatic group, it may have the formula —$(CH_2)_a$—O—$(CH_2)_b$—O—$(CH_2)_c$—, wherein each of a, b, and c is independently from 1 to about 7.

When M is a branched or straight chain thiaaliphatic group, the group may be any of the preceding oxaaliphatic groups wherein the oxygen atoms are replaced by sulfur atoms.

When M is a branched or straight chain, aza-aliphatic group having from 1 to about 20 carbon atoms, it may be a divalent group such as —$CH_2NH$—, —$(CH_2)_2N$—, —$CH_2(C_2H_5)N$—, -n-$C_4H_9NH$—, -t-$C_4H_9NH$—, —$CH_2(C_3H_7)N$—, —$C_2H_5(C_2H_5)N$—, —$CH_2(C_8H_{17})N$—, —$CH_2NHCH_2$—, —$(CH_2)_2NCH_2$—, —$CH_2(C_2H_5)NCH_2CH_2$—, -n-$C_4H_9NHCH_2$—, -t-$C_4H_9NHCH_2CH_2$—, —$CH_2(C_3H_7)N(CH_2)_4$—, —$C_2H_5(C_2H_5)NCH_2$—, —$CH_2(C_8H_{17})NCH_2CH_2$—, and the like. When M is a branched or straight chain, amino-aliphatic group, it may have the formula —$(CH_2)_aNR1$- or —$(CH_2)_aN(R1)(CH_2)_b$— where R1 is —H, aryl, alkenyl or alkyl and each of a and b is independently from about 1 to about 7.

When M is a branched or straight-chain carboxylalkyl group having from 1 to about 20 carbon atoms, it may be, for example, carboxymethyl, carboxymethyl, 2-carboxyethyl, 1-carboxyethyl, 3-carboxypropyl, 4-carboxybutyl, 5-carboxypentyl, 6-carboxyhexyl, 1,1-dimethyl-2-carboxyethyl, 2-methyl-3-carboxylpropyl, and the like. Alternatively, any structure represented by the formulas —$(CH_2)_a$—$CO_2$—, wherein a is about 1 to about 7, or —$CO_2$—$(CH_2)_b$—, wherein b is about 1 to about 7.

When M is a branched or straight-chain alkoxycarbonyl-substituted alkyl group, it may be, for example, methoxycarbonylmethyl, 3-methoxycarbonypropyl, ethoxycarbonylmethyl, 3-ethoxycarbonylpropyl, 4-ethoxycarbonylbutyl, 5-isopropoxycarbonylpentyl, 6-propoxycarbonylhexyl, 1,1-dimethyl-2-butoxycarbonylethyl, 2-methyl-3-tert-butoxycarbonylpropyl, 2-pentyloxycarbonylethyl, hexyloxycarbonylmethyl, and the like, or, alternatively, any structure represented by the formula —$(CH_2)_a$—$CO_2$—$(CH_2)_b$— wherein each of a and b, independently, is about 1 to about 7. In certain embodiments, M may be any of the preceding alkoxycarbonyl-subsituted alkyl groups wherein the oxygen atoms are replaced by sulfur atoms.

In certain embodiments, each constitutional unit $t_s$ may be repeated in a sequence, e.g., alternating, in blocks (which may themselves repeat), or in any other pattern or random arrangement. Each constitutional unit $t_s$ may repeat any number of times, and one unit may occur with substantially the same frequency, more often, or less often than another unit, such that both units may be present in approximately the same amount, or in differing amounts, which may differ slightly or be highly disparate, e.g., one unit is present nearly to the exclusion of the other. In certain embodiments, the chiral centers of each unit (if any) may be the same or different and may be arranged in an orderly fashion or in a random sequence.

In certain embodiments, $n_s$ and x of Formula II represents an integer in the range of about 1 to about 1000 or more, e.g., about 1, about 5, about 10, about 20, about 50, about 100, about 250, about 500, about 750, about 1000, etc.

In certain embodiments, the number of constitutional units (whether the same or different) in Formula II that make up the polymeric chain may range over a wide range, e.g., from about 1 to 25,000. In certain embodiments, the number of constitutional units may be about 1, 5, 10, 15 or 30.

The above Formula II encompass a variety of different polymeric or oligomeric structures, including block copolymers, random copolymers, random terpolymers and segregated block copolymers and terpolymers, all of which are contemplated by the present invention.

Additional non-limiting structures for polymer chains R1 derived from Formula II are set forth below in FIGS. IIa-f.

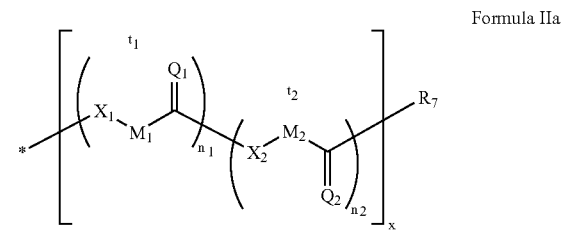

Formula IIa wherein, x is an integer equal to at least 1 or more;

$n_1$ and $n_2$ are equal to 1;

the $t_1$ and $t_2$ units may be in any order for each occurrence of the unit x; and all other moieties are defined above.

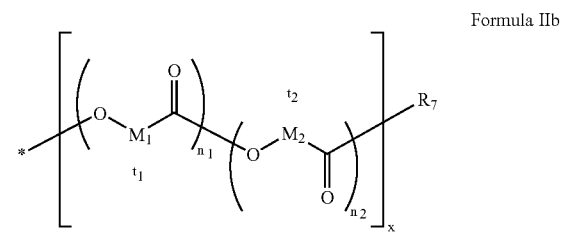

Formula IIb wherein,

M1 and M2, each independently, may be selected from the group consisting of —$CH(CH_3)$—; —$CH(CH_3)CO_2CH(CH_3)$—; —$(CH_2)_d$—; and —$(CH_2)_d$—O—; wherein d is from 1 to about 12;

$n_1$ and $n_2$ are equal to 1;

the $t_1$ and $t_2$ units may be in any order for each occurrence of the unit x;

x is an integer from 1 to about 20; and all other moieties are defined above.

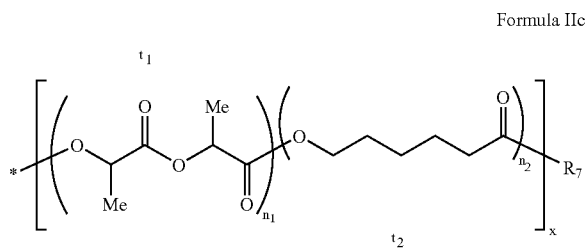

Formula IIc wherein,

R7 represents —O—$(CH_2)_mCH_3$ or —O—$(CH_2CH_2O)_mCH_3$, wherein m is at least 1;

$n_1$ and $n_2$ are on average for each polymeric chain in the compound equal to about 2 and 2 or about 5.5 and 1.8, respectively;

the $t_1$ and $t_2$ units may be in any order for each occurrence of the unit x;

x is equal to 1; and all other moieties are defined above.

Formula IId

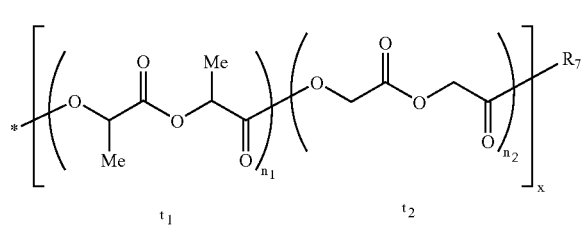

wherein,

R7 represents —O—$(CH_2)_m CH_3$, wherein m is at least 1;

$n_1$ and $n_2$ are on average for each unit x are equal to about 2.4 and 1.6, respectively;

the $t_1$ and $t_2$ units may be in any order for each occurrence of the unit x;

x is at least 1; and all other moieties are defined above.

Formula IIe

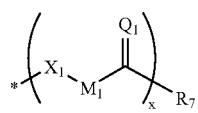

wherein, x is an integer equal to at least 2; and all other moieties are defined above.

Formula IIf

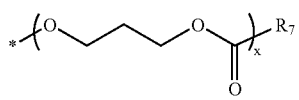

wherein,

R7 represents —O—$(CH_2)_m CH_3$, wherein m is at least 1; and x is at least 2; and all other moieties are defined above.

The polymeric chains may be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

For example, in certain embodiments of the R1 polymeric chains depicted by Formulae II and IIa-f, the chirality of each constitutional unit comprised of a different $M_s$ group is identical, whereas in other embodiments, the chirality is different. By way of example but not limitation, in Formula IIb above when $M_1$ and $M_2$ are both —$CH(CH_3)$—, if the chiral centers for both $M_1$ and $M_2$ are the D-enantiomers or the L-enantiomers, then the polymeric chain is effectively equivalent to D-lactic acid or L-lactic acid, respectively, thereby giving rise to a region similar to poly(D-lactic acid) or poly (L-lactic acid), respectively. Conversely, again when $M_1$ and $M_2$ are both —$CH(CH_3)$—, if the chiral centers of the two units alternate D- and L-enantiomers (e.g., one unit of D-enantiomer, one unit of L-enantiomer, etc.), then the resulting polymeric chain is analogous to poly(meso-lactic acid) (i.e., a polymer formed by polymerization of meso-lactide).

As exemplified above, the type and ratio of different constitutional units in any polymeric chain R1 may vary. For example, in certain embodiments, the polymeric R1 chains may be composed almost entirely, if not entirely, of a single constitutional unit, such as depicted in Formula IIe. Alternatively, in other instances, the polymeric chains are composed of two different types of constitutional units, in which the percentage of each subunit may vary from less than 1:99 to more than 99:1, or alternatively 10:90, 15:85, 25:75, 40:60, 50:50, 60:40, 75:25, 85:15, 90:10 or the like. In other embodiments, in which three or more different types of constitutional units are present in a polymeric R1 chain, the present invention contemplates a range of mixtures like those taught for the two-unit systems. The amounts of the different units in polymeric chains with multiple units may be expressed as an average for all the polymeric chains in the subject phosphorus-containing compound.

In certain embodiments, the subject phosphorus-containing compounds are soluble in one or more common organic solvents for ease of fabrication and processing. Common organic solvents include such solvents as chloroform, dichloromethane, dichloroethane, 2-butanone, butyl acetate, ethyl butyrate, acetone, ethyl acetate, dimethylacetamide, N-methyl pyrrolidone, dimethylformamide, and dimethylsulfoxide.

In certain embodiments, the subject phosphorus-containing compounds have weight-averaged molecular weights ranging from about 1000 or up to about 350,000 daltons, or alternatively from about 2,500, 3,000, 4,000, 5,000, 10,000, 15,000, 20,000, 25,000, 30,000, 40,000, 50,000,60,000, 70,000, 80,000, 90,000, 100,000, 125,000, 150,000, 175,000, 200,000, 225,000, 250,000, 275,000, 300,000 to 325,000 daltons. Number-average molecular weight (Mn) may also vary widely, but generally fall in the range described above. Within a given sample of a subject polymer, a wide range of molecular weights may be present. For example, molecules within the sample may have molecular weights which differ by a factor of 2, 5, 10, 20, 50, 100, or more, or which differ from the average molecular weight by a factor of 2, 5, 10, 20, 50, 100, or more. One method to determine molecular weight is by gel permeation chromatography ("GPC"), e.g., mixed bed columns, $CH_2Cl_2$ solvent, light scattering detector, and off-line dn/dc. Other methods are known to those of skill in the art.

D. Exemplary Methods of Making the Subject Phosphorus-Containing Compounds

The subject phosphorus-containing compounds may be prepared by a variety of methods known to those of skill in the art. For example, in certain embodiments, the subject phosphorus-containing compounds may be prepared by reaction of a chemical moiety containing the central phosphorus atom with one or more precursors to the polymeric chains in a condensation reaction. In such a condensation reaction, the subject phosphorus-containing compound contains fewer atoms than reactants. The extra atoms are eliminated in a small molecule by-product of the polymerization reaction, often water, but also other molecules such as hydrochloric acid, etc.

Exemplary schematic reactions are shown below:

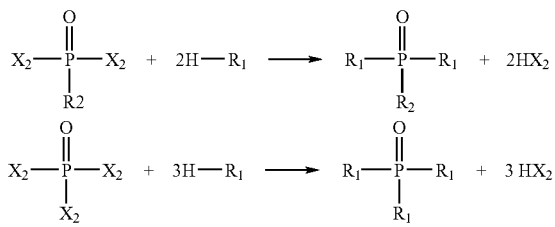

R2 is as defined above. In certain embodiments, X2 is a halogen, often chlorine. H—R1 is the precursor to the polymeric chain, with the * depicted in Formula II replaced with a hydrogen atom in the precursor. The number of polymeric chains in the resulting phosphorus-containing compound are determined by the number of X2 groups on the phosphorus-containing reactant. The presence of a non-reactive cap R7 at the terminus of the polymeric chain precursor prevents further condensation with another phosphorus-containing reactant. Examples of these reactions are described below.

Although the above reaction may take place in bulk, in solution, by interfacial condensation and the like, in many instant embodiments, the process takes place under solution conditions. Particularly useful solvents include methylene chloride, chloroform, tetrahydrofuran, di-methyl formamide, dimethyl sulfoxide or any of a wide variety of other inert organic solvents. Solution polycondensation requires that both the polymeric chain precursor and the phosphorus-containing reactance be sufficiently soluble in a common solvent. The solution polymerization is generally run in the presence of an excess of an acid acceptor and a catalyst, such as DMAP. Useful acid acceptors include tertiary amines as pyridine or triethylamine.

In general, subject phosphorus-containing compounds of the present invention may be isolated from the reaction mixture by conventional techniques, such as by precipitating out, extraction with an immiscible solvent, evaporation, filtration, crystallization and the like.

The precursors to the polymeric chains may be prepared by a variety of methods known to those of skill in the art, including condensation reactions and ring-opening polymerizations. Examples of such reactions are described below. The stoichiometry of the reaction is an important factor in determining the molecular weights of the polymeric chain precursor.

By way of example, the polymeric chain precursors of Formula II and IIa-f may be prepared using a cyclic compound and initiator HQ-R7 as follows:

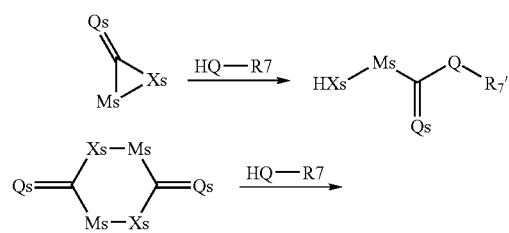

-continued

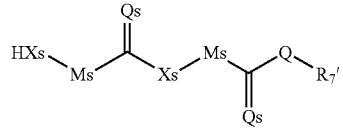

wherein all the moieties are defined above. After the initial ring opening shown above upon reaction of the nucleophile of the initiator with the electrophile of the cyclic reactant, the polymeric chain precursor may be extended by reacting the protonated nucleophile HXs-with another electrophile, in this example —C(=Qs)-Xs-, of either the same cyclic compound or a different cyclic compound. Variation of the ratio of two or more cyclic compounds in a reaction mixture will vary the amount and sequence of the different constitutional units that ultimately are found in the polymeric chain precursor. Additional phosphorus linkages may be incorporated along the polymeric chain precursor chain by condensation of a phospho-Halogenate in the growing polymeric chain precursor, as long as the final polymeric chain precursor has only one reactive nucleophile for reaction with the phosphorus-containing reactant to produce the subject phosphorus-containing compounds.

The time required for the synthetic processes described herein may vary widely, depending on the type of reaction being used, the molecular weight desired and, in general, the need to use more or less rigorous conditions for the reaction to proceed to the desired degree of completion.

E. Therapeutic Agents and Subject Compositions

In one aspect of this invention, a composition comprising a subject phosphorus-containing compound and one or more therapeutic agents may be prepared. The therapeutic agent may vary widely with the intended purpose for the composition. The term "therapeutic agent" is art-recognized and refers to any chemical moiety that is a biologically, physiologically, or pharmacologically active substance that acts locally or systemically in a subject Examples of therapeutic agents, also referred to as "drugs", are described in well-known literature references such as the Merck Index, the Physicians Desk. Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject.

In certain embodiments, the subject compositions comprise about 5% to about 75% or more by weight of the total composition, alternatively about 10%, 20%, 30%, 40%, 50%, 60% or 70%, of a therapeutic agent.

Non-limiting examples of therapeutic agents include the following: adrenergic blocking agents, anabolic agents, androgenic steroids, antacids, anti-asthmatic agents, anti-allergenic materials, anti-cholesterolemic and anti-lipid agents, anti-cholinergics and sympathornimetics, anti-coagulants, anti-convulsants, anti-diarrheals, anti-emetics, anti-hypertensive agents, anti-infective agents, anti-inflammatory agents such as steroids, non-steroidal anti-inflammatory agents, anti-malarials, anti-manic agents, anti-nauseants, anti-neoplastic agents, anti-obesity agents, anti-parkinsonian agents, anti-pyretic and analgesic agents, anti-spasmodic agents, anti-thrombotic agents, anti-uricemic agents, anti-anginal agents, antihistamines, anti-tussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, humoral agents, hyperglycemic agents, hypnotics, hypoglycemic agents, ion exchange resins, laxatives, mineral supplements, miotics, mucolytic agents, neuromuscular drugs, nutritional substances, peripheral vasodilators, progestational agents, prostaglandins, psychic energizers, psychotropics, sedatives, stimulants, thyroid and anti-thyroid agents, tranquilizers, uterine relaxants, vitamins, antigenic materials, and pro-drugs.

Specific examples of useful therapeutic agents from the above categories include: (a) anti-neoplastics such as androgen inhibitors, antimetabolites, cytotoxic agents, and immunomodulators; (b) anti-tussives such as dextromethorphan, dextromethorphan hydrobromide, noscapine, carbetapentane citrate, and chlophedianol hydrochloride; (c) antihistamines such as chlorpheniramine maleate, phenindamine tartrate, pyrilamine maleate, doxylamine succinate, and phenyltoloxamine citrate; (d) decongestants such as phenylephrine hydrochloride, phenylpropanolamine hydrochloride, pseudoephedrine hydrochloride, and ephedrine; (e) various alkaloids such as codeine phosphate, codeine sulfate, and morphine; (f) mineral supplements such as potassium chloride, zinc chloride, calcium carbonate, magnesium oxide, and other alkali metal and alkaline earth metal salts; (g) ion exchange resins such as cholestyramine; (h) anti-arrhythmics such as N-acetylprocainamide; (i) antipyretics and analgesics such as acetaminophen, aspirin and ibuprofen; (j) appetite suppressants such as phenyl-propanolamine hydrochloride or caffeine; k) expectorants such as guaifenesin; (l) antacids such as aluminum hydroxide and magnesium hydroxide; (m) biologicals such as peptides, polypeptides, proteins and amino acids, hormones, interferons or cytokines and other bioactive peptidic compounds, such as hGH, tPA, calcitonin, ANF, EPO and insulin; (n) anti-infective agents such as anti-fungals, anti-virals, antiseptics and antibiotics; and (m) desensitizing agents and antigenic materials, such as those useful for vaccine applications.

More specifically, non-limiting examples of useful therapeutic agents include the following therapeutic categories: analgesics, such as nonsteroidal anti-inflammatory drugs, opiate agonists and salicylates; antihistamines, such as $H_1$-blockers and $H_2$-blockers; anti-infective agents, such as antihelmintics, antianaerobics, antibiotics, aminoglycoside antibiotics, antifungal antibiotics, cephalosporin antibiotics, macrolide antibiotics, miscellaneous β-lactam antibiotics, penicillin antibiotics, quinolone antibiotics, sulfonamide antibiotics, tetracycline antibiotics, antimycobacterials, anti-tuberculosis antimycobacterials, antiprotozoals, antimalarial antiprotozoals, antiviral agents, anti-retroviral agents, scabicides, and urinary anti-infectives; antineoplastic agents, such as alkylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics; autonomic agents, such as anticholinergics, antimuscarinic anticholinergics, ergot alkaloids, parasympathomimetics, cholinergic agonist parasympathomimetics, cholinesterase inhibitor parasympathomimetics, sympatholytics, α-blocker sympatholytics, β-blocker sympatholytics, sympathomimetics, and adrenergic agonist sympathomimetics; cardiovascular agents, such as antianginals, β-blocker antianginals, calcium-channel blocker antianginals, nitrate antianginals, antiarrhythmics, cardiac glycoside antiarrhythmics, class I antiarrhythmics, class II antiarrhythmics, class III antiarrhythmics, class IV antiarrhythmics, antihypertensive agents, α-blocker antihypertensives, angiotensin-converting enzyme inhibitor (ACE inhibitor) antihypertensives, β-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, HMG-CoA reductase inhibitor antilipemics, inotropes, cardiac glycoside inotropes, and thrombolytic agents; dermatological agents, such as antihistamines, anti-inflammatory agents, corticosteroid anti-inflammatory agents, antipruritics/local anesthetics, topical anti-infectives, antifungal topical anti-infectives, antiviral topical anti-infectives, and topical antineoplastics; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, $H_2$-blocker anti-ulcer agents, cholelitholytic agents, digestants, emetics, laxatives and stool softeners, and prokinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hematological agents, such as antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, such as abortifacients, adrenal agents, corticosteroid adrenal agents, androgens, anti-androgens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, anti-thyroid agents, thyroid hormones, and tocolytics; immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, gold compound anti-inflammatory agents, immunosuppressive anti-inflammatory agents, nonsteroidal anti-inflammatory drugs (NSAIDs), salicylate anti-inflammatory agents, skeletal muscle relaxants, neuromuscular blocker skeletal muscle relaxants, and reverse neuromuscular blocker skeletal muscle relaxants; neurological agents, such as anticonvulsants, barbiturate anticonvulsants, benzodiazepine anticonvulsants, anti-migraine agents, anti-parkinsonian agents, anti-vertigo agents, opiate agonists, and opiate antagonists; ophthalmic agents, such as anti-glaucoma agents, β-blocker anti-glaucoma agents, miotic anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic anti-inflammatory agents, ophthalmic corticosteroid anti-inflammatory agents, and ophthalmic nonsteroidal anti-inflammatory drugs (NSAIDs); psychotropic agents, such as antidepressants, heterocyclic antidepressants, monoamine oxidase inhibitors (MAOIs), selective serotonin re-uptake inhibitors (SSRIs), tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, such as antitussives, bronchodilators, adrenergic agonist bronchodilators, antimuscarinic bronchodilators, expectorants, mucolytic agents, respiratory anti-inflammatory agents, and respiratory corticosteroid anti-inflammatory agents; toxicology agents, such as antidotes, heavy metal antagonists/chelating agents, substance abuse agents, deterrent substance abuse agents, and withdrawal substance abuse agents; minerals; and vitamins, such as vitamin A, vitamin B, vitamin C, vitamin D, vitamin E, and vitamin K.

Other classes of therapeutic agents from the above categories include: (1) analgesics in general, such as lidocaine, other caine analgesics or derivatives thereof, and nonsteroidal anti-inflammatory drugs NSAIDs) analgesics, including diclofenac, ibuprofen, ketoprofen, and naproxen; (2) opiate agonist analgesics, such as codeine, fentanyl, hydromorphone, and morphine; (3) salicylate analgesics, such as aspirin (ASA) (enteric coated ASA); (4) $H_1$-blocker antihistamines, such as clemastine and terfenadine; (5) $H_2$-blocker antihistamines, such as cimetidine, famotidine, nizadine, and ranitidine; (6) anti-infective agents, such as mupirocin; (7) antianaerobic anti-infectives, such as chloramphenicol and clindamycin; (8) antifungal antibiotic anti-infectives, such as amphotericin b, clotrimazole, fluconazole, and ketoconazole; (9) macrolide antibiotic anti-infectives, such as azithromycin and erythromycin; (10) miscellaneous B-lactam antibiotic anti-infectives, such as aztreonam and imipenem; (11) penicillin antibiotic anti-infectives, such as nafcillin, oxacillin, penicillin G, and penicillin V; (12) quinolone antibiotic anti-infectives, such as ciprofloxacin and norfloxacin; (13) tetracycline antibiotic anti-infectives, such as doxycycline, minocycline, and tetracycline; (14) antituberculosis antimycobacterial anti-infectives such as isoniazid (INH), and rifampin; (15) antiprotozoal anti-infectives, such as atovaquone and dapsone; (16) antimalarial antiprotozoal anti-infectives, such as chloroquine and pyrimethamine; (17) antiretroviral anti-infectives, such as ritonavir and zidovudine; (18) antiviral anti-infective agents, such as acyclovir, ganciclovir, interferon alfa, and rimantadine; (19) alkylating antineoplastic agents, such as carboplatin and cisplatin; (20) nitrosourea alkylating antineoplastic agents, such as carmustine (BCNU); (21) antimetabolite antineoplastic agents, such as methotrexate; (22) pyrimidine analog antimetabolite antineoplastic agents, such as fluorouracil (5-FU) and gemcitabine; (23) hormonal antineoplastics, such as goserelin, leuprolide, and tamoxifen; (24) natural antineoplastics, such as aldesleukin, interleukin-2, docetaxel, etoposide (VP-16), interferon alfa, paclitaxel, other taxane derivatives, and tretinoin (ATRA); (25) antibiotic natural antineoplastics, such as bleomycin, dactinomycin, daunorubicin, doxorubicin, and mitomycin; (26) vinca alkaloid natural antineoplastics, such as vinblastine and vincristine; (27) autonomic agents, such as nicotine; (28) anticholinergic autonomic agents, such as benztropine and trihexyphenidyl; (29) antimuscarinic anticholinergic autonomic agents, such as atropine and oxybutynin; (30) ergot alkaloid autonomic agents, such as bromocriptine; (31) cholinergic agonist parasympathomimetics, such as pilocarpine; (32) cholinesterase inhibitor parasympathomimetics, such as pyridostigmine; (33) α-blocker sympatholytics, such as prazosin; (34) β-blocker sympatholytics, such as atenolol; (35) adrenergic agonist sympathomimetics, such as albuterol and dobutamine; (36) cardiovascular agents, such as aspirin (ASA) (enteric coated ASA); (37) β-blocker antianginals, such as atenolol and propranolol; (38) calcium-channel blocker antianginals, such as nifedipine and verapamil; (39) nitrate antianginals, such as isosorbide dinitrate (ISDN); (40) cardiac glycoside antiarrhythmics, such as digoxin; (41) class I antiarrhythmics, such as lidocaine, mexiletine, phenytoin, procainamide, and quinidine; (42) class II antiarrhythmics, such as atenolol, metoprolol, propranolol, and timolol; (43) class III antiarrhythmics, such as amiodarone; (44) class IV antiarrhythmics, such as diltiazem and verapamil; (45) β-blocker antihypertensives, such as prazosin; (46) angiotensin-converting enzyme inhibitor (ACE inhibitor) antihypertensives, such as captopril and enalapril; (47) β-blocker antihypertensives, such as atenolol, metoprolol, nadolol, and propanolol; (48) calcium-channel blocker antihypertensive agents, such as diltiazem and nifedipine; (49) central-acting adrenergic antihypertensives, such as clonidine and methyldopa; (50) diurectic antihypertensive agents, such as amiloride, furosemide, hydrochlorothiazide (HCTZ), and spironolactone; (51) peripheral vasodilator antihypertensives, such as hydralazine and minoxidil; (52) antilipemics, such as gemfibrozil and probucol; (53) bile acid sequestrant antilipemics, such as cholestyramine; (54) HMG-CoA reductase inhibitor antilipemics, such as lovastatin and pravastatin; (55) inotropes, such as amrinone, dobutamine, and dopamine; (56) cardiac glycoside inotropes, such as digoxin; (57) thrombolytic agents, such as alteplase (TPA), anistreplase, streptokinase, and urokinase; (58) dermatological agents, such as colchicine, isotretinoin, methotrexate, minoxidil, tretinoin (ATRA); (59) dermatological corticosteroid anti-inflammatory agents, such as betamethasone and dexamethasone; (60) antifungal topical anti-infectives, such as amphotericin B, clotrimazole, miconazole, and nystatin; (61) antiviral topical anti-infectives, such as acyclovir; (62) topical antineoplastics, such as fluorouracil (5-FU); (63) electrolytic and renal agents, such as lactulose; (64) loop diuretics, such as furosemide; (65) potassium-sparing diuretics, such as triamterene; (66) thiazide diuretics, such as hydrochlorothiazide (HCTZ); (67) uricosuric agents, such as probenecid; (68) enzymes such as RNase and DNase; (69) thrombolytic enzymes, such as alteplase, anistreplase, streptokinase and urokinase; (70) antiemetics, such as prochlorperazine; (71) salicylate gastrointestinal anti-inflammatory agents, such as sulfasalazine; (72) gastric acid-pump inhibitor anti-ulcer agents, such as omeprazole; (73) $H_2$-blocker anti-ulcer agents, such as cimetidine, famotidine, nizatidine, and ranitidine; (74) digestants, such as pancrelipase; (75) prokinetic agents, such as erythromycin; (76) opiate agonist intravenous anesthetics such as fentanyl; (77) hematopoietic antianemia agents, such as erythropoietin, filgrastim (G-CSF), and sargramostim (GM-CSF); (78) coagulation agents, such as antihemophilic factors 1-10 (AHF 1-10); (79) anticoagulants, such as warfarin; (80) thrombolytic enzyme coagulation agents, such as alteplase, anistreplase, streptokinase and urokinase; (81) hormones and hormone modifiers, such as bromocriptine; (82) abortifacients, such as methotrexate; (83) antidiabetic agents, such as insulin; (84) oral contraceptives, such as estrogen and progestin; (85) progestin contraceptives, such as levonorgestrel and norgestrel; (86) estrogens such as conjugated estrogens, diethylstilbestrol (DES), estrogen (estradiol, estrone, and estropipate); (87) fertility agents, such as clomiphene, human chorionic gonadotropin (HCG), and menotropins; (88) parathyroid agents such as calcitonin; (89) pituitary hormones, such as desmopressin, goserelin, oxytocin, and vasopressin (ADH); (90) progestins, such as medroxyprogesterone, norethindrone, and progesterone; (91) thyroid hormones, such as levothyroxine; (92) immunobiologic agents, such as interferon beta-1b and interferon gamma-1b; (93) immunoglobulins, such as immune globulin IM, IMIG, IGIM and immune globulin IV, IVIG, IGIV; (94) amide local anesthetics, such as lidocaine; (95) ester local anesthetics, such as benzocaine and procaine; (96) musculoskeletal corticosteroid anti-inflammatory agents, such as beclomethasone, betamethasone, cortisone, dexamethasone, hydrocortisone, and prednisone; (97) musculoskeletal anti-inflammatory immunosuppressives, such as azathioprine, cyclophosphamide, and methotrexate; (98) musculoskeletal nonsteroidal anti-inflammatory drugs (NSAIDs), such as diclofenac, ibuprofen, ketoprofen, ketorlac, and naproxen; (99) skeletal muscle relaxants, such as baclofen, cyclobenzaprine, and diazepam; (100) reverse neuromuscular blocker skeletal muscle relaxants, such as pyridostigmine; (101) neurological agents, such as nimodipine, riluzole, tacrine and ticlopidine; (102) anticonvulsants, such as carbamazepine, gabapentin, lamotrigine, phenytoin, and valproic acid; (103) barbiturate anticonvulsants, such as phenobarbital and primidone; (104) benzodiazepine anticonvulsants, such as clonazepam, diazepam, and lorazepam; (105) anti-parkinsonian agents, such as bromocriptine, levodopa, carbidopa, and pergolide; (106) anti-vertigo agents, such as meclizine; (107) opiate agonists, such as codeine, fentanyl, hydromorphone, methadone, and morphine; (108) opiate antagonists, such as naloxone; (109) β-blocker anti-glaucoma agents, such as timolol; (110) miotic anti-glaucoma agents, such as pilocarpine; (111) ophthalmic aminoglycoside anti-infectives, such as gentamicin, neomycin, and tobramycin; (112) ophthalmic quinolone anti-infectives, such as ciprofloxacin, norfloxacin, and ofloxacin; (113) ophthalmic corticosteroid anti-inflammatory agents, such as dexamethasone and prednisolone; (114) ophthalmic nonsteroidal anti-inflammatory drugs (NSAIDs), such as diclofenac; (115) antipsychotics, such as clozapine, haloperidol, and risperidone; (116) benzodiazepine anxiolytics, sedatives and hypnotics, such as clonazepam, diazepam, lorazepam, oxazepam, and prazepam; (117) psychostimulants, such as methylphenidate and pemoline; (118) antitussives, such as codeine; (119) bronchodilators, such as theophylline; (120) adrenergic agonist bronchodilators, such as albuterol; (121) respiratory corticosteroid anti-inflammatory agents, such as dexamethasone; (122) antidotes, such as flumazenil and naloxone; (123) heavy metal antagonists/chelating agents, such as penicillamine; (124) deterrent substance abuse agents, such as disulfiram, naltrexone, and nicotine; (125) withdrawal substance abuse agents, such as bromocriptine; (126) minerals, such as iron, calcium, and magnesium; (127) vitamin B compounds, such as cyanocobalamin (vitamin $B_{12}$) and niacin (vitamin $B_3$); (128) vitamin C compounds, such as ascorbic acid; and (129) vitamin D compounds, such as calcitriol.

Further, recombinant or cell-derived proteins may be used, such as: recombinant beta-glucan; bovine immunoglobulin concentrate; bovine superoxide dismutase; the formulation comprising fluorouracil, epinephrine, and bovine collagen; recombinant hirudin (r-Hir), HIV-1 immunogen; recombinant human growth hormone (r-hGH); recombinant EPO (r-EPO); gene-activated EPO (GA-EPO); recombinant human hemoglobin (r-Hb); recombinant human mecasermin (r-IGF-1); recombinant interferon beta-1a; lenograstim (G-CSF); olanzapine; recombinant thyroid stimulating hormone (r-TSH); and topotecan.

Still further, the following listing of peptides, proteins, and other large molecules may also be used, such as interleukins 1 through 18, including mutants and analogues; interferons α, γ, and β; luteinizing hormone releasing hormone (LHRH) and analogues, gonadatropin releasing hormone (GnRH), transforming growth factor-α (TGF-α); fibroblast growth factor (FGF); tumor necrosis factor-α & γ (TNF-α and γ); nerve growth factor (NGF); growth hormone releasing factor (GHRF); epidermal growth factor (EGF); fibroblast growth factor homologous factor (FGFHF); hepatocyte growth factor (HGF); insulin growth factor (IGF); invasion inhibiting factor-2 (IIF-2); bone morphogenetic proteins 1-7 (BMP 1-7); somatostatin; thymosin-α-1; γ-globulin; superoxide dismutase (SOD); and complement factors.

The term "therapeutic agent" includes those agents that may be used for diagnostic purposes. Examples of such diagnostic agents include imaging agents that are capable of generating a detectable image shall include radionuclides and compounds containing them (e.g., tritium, iodine-125, iodine-131, iodine-123, iodine-124, astatine-210, carbon-11, carbon-14, nitrogen-13, fluorine-18, Tc-99m, Re-186, Ga-68, Re-188, Y-90, Sm-153, Bi-212, Cu-67, Cu-64, and Cu-62, to name a few), unpair spin atoms and free radicals (e.g., Fe, lanthanides, and Gd), contrast agents (e.g., chelated (DTPA) manganese), and fluorescent or chemiluminescent agents.

Various forms of the therapeutic agents may be used. These include, without limitation, such forms as uncharged molecules, molecular complexes, salts, ethers, esters, amides, and the like, which are biologically activated when implanted, injected or otherwise placed into a subject.

In certain embodiments, other materials may be incorporated into subject compositions in addition to one or more therapeutic agents. For example, plasticizers and stabilizing agents known in the art may be incorporated in compositions of the present invention. In certain embodiments, additives such as plasticizers and stabilizing agents are selected for their biocompatibility.

A composition of this invention may further contain one or more adjuvant substances, such as fillers, thickening agents or the like. In other embodiments, materials that serve as adjuvants may be associated with the composition. Such additional materials may affect the characteristics of the composition that results. For example, fillers, such as bovine serum albumin (BSA) or mouse serum albumin (MSA), may be associated with the polymer composition. In certain embodiments, the amount of filler may range from about 0.1 to about 50% or more by weight of the composition, or about 2.5, 5, 10, 25, 40 percent. Incorporation of such fillers may affect the sustained release rate of any encapsulated substance. Other fillers known to those of skill in the art, such as carbohydrates, sugars, starches, saccharides, celluloses and polysaccharides, including mannitose and sucrose, may be used in certain embodiments in the present invention.

Buffers, acids and bases may be incorporated in the compositions to adjust their pH. Agents to increase the diffusion distance of agents released from the composition may also be included.

The charge, lipophilicity or hydrophilicity of any subject composition may be modified by employing an additive. For example, surfactants may be used to enhance miscibility of poorly miscible liquids. Examples of suitable surfactants include dextran, polysorbates, and sodium lauryl sulfate. In general, surfactants are used in low concentrations, generally less than about 5%.

F. Biodegradability and Release Characteristics for Subject Compositions

In certain embodiments, the subject phosphorus-containing compounds, upon contact with body fluids, undergo gradual degradation. The life of such a compound in vivo depends, among other things, upon its molecular weight, viscosity, biostability, and the like. In general, the greater the molecular weight, viscosity, and biostability, the slower biodegradation will be.

In certain embodiments, the subject phosphorus-containing compounds biodegrade within a period that is acceptable in the desired application. In certain embodiments, such as in vivo therapy, such degradation occurs in a period usually less than about five years, one year, six months, three months, one month, fifteen days, five days, three days, or even one day on exposure to a physiological solution with a pH between 6 and 8 having a temperature of between 25 and 37° C. In other embodiments, the subject phosphorus-containing compound degrades in a period of between about one hour and several weeks, depending on the desired application.

If a subject phosphorus-containing compound is formulated with a therapeutic agent or other material, release of such an agent or other material for a sustained or extended period as compared to the release from an isotonic saline solution generally results. Such release profile may result in prolonged delivery (over, for example, 2 to 500 hours, or 4 to 200 hours) of effective amounts (e.g., 0.00001 mg/kg/hour to 10 mg/kg/hour) of the therapeutic agent or any other material associated with the polymer.

A variety of factors may affect the rate and extent of release. Some of such factors include: the selection of the various substituent groups, the enantiomeric or diastereomeric purity of the polymeric chains, homogeneity of monomeric subunits found in the polymeric chains, and the length of the polymeric chains.

One protocol generally accepted in the field that may be used to determine the release rate of any therapeutic agent or other material loaded in the compositions of the present invention involves degradation of any such composition in a 0.1 M phosphate-buffered saline (PBS) solution (pH 7.4) at 37° C., an assay known in the art. For purposes of the present invention, the term "PBS protocol" is used herein to refer to such protocol.

In certain instances, the release rates of different compositions of the present invention may be compared by subjecting them to such a protocol. In certain instances, it may be necessary to process compositions in the same fashion to allow direct and relatively accurate comparisons of different systems to be made. Such comparisons may indicate that any one composition releases incorporated material at a rate from about 2 or less to about 1000 or more times faster than another drug delivery system. Alternatively, a comparison may reveal a rate difference of about 3, 5, 7, 10, 25, 50, 100, 250, 500 or 750. Even higher rate differences are contemplated by the present invention and release rate protocols.

The release rate of any incorporated material may also be characterized by the amount of such material released per day per mg of a subject phosphorus-containing compound or therapeutic composition. For example, in certain embodiments, the release rate may vary from about 1 ng or less of any incorporated material per day per mg of compound or composition to about 5000 or more ng/day·mg. Alternatively, the release rate maybe about 10, 25, 50, 75, 100, 125, 150, 175, 200, 250, 300, 350, 400, 450, 500, 600, 700, 800 or 900 ng/day·mg. In still other embodiments, the release rate of any incorporated material may be 10,000 ng/day·mg or even higher.

In another aspect, the rate of release of any material from any subject phosphorus-containing compound or composition of the present invention may be presented as the half-life of such material in the such matrix.

In addition to the embodiment involving protocols for in vitro determination of release rates, in vivo protocols, whereby in certain instances release rates for compositions may be determined in vivo, are also contemplated by the present invention. Other assays useful for determining the release of any material from the compositions of the present system are known in the art.

G. Amphiphilic Subject Compounds and Reverse Thermal Gelation

Certain of the subject phosphorus containing compounds may be amphiphilic in nature, i.e., they have a polar or hydrophobic region and a non-polar or hydrophilic region. Further, the subject phosphorus containing compounds may have more than two polar and non-polar regions. For example, a subject phosphorus containing compound may have a two polar regions separated by a nonpolar region, like a block polymer. Certain of those molecules may exhibit reverse thermal gelation, which is discussed in greater detail below.

Subject amphiphilic compounds may have a number of different structures. For example, R1 may be hydrophobic and R2 hydrophilic, or vice-versa. Alternatively, R1 may be hydrophobic or hydrophilic, and R7, which is bound to the end of the polymer chain found in R1, would be the opposite. Examples of this latter structural type are described in Example 9 below.

Certain of the subject phosphorus-containing compounds exhibit reverse thermal gelation. Usually, such compounds will be amphiphilic in nature.

The gelation temperature of the subject phosphorus-containing compounds may vary widely. In certain embodiments, the gelation temperature of the subject phosphorus-containing compounds in solution may be low enough to keep the composition of the invention liquid, e.g., at room temperature and/or at body temperature. Then, the gelation temperature of the subject phosphorus-containing compounds in solution is below about 37 ° C., or alternatively below about 25° C., or even below about 0° C., e.g., between about −60° C and 37° C., between about −50° C. and 0° C., etc. (provided that the gelation temperature does not fall below the freezing point of the mixture). Even in those cases when a liquid composition is desired, solutions of subject phosphorus-containing compounds having higher gelation temperatures, e.g., above body temperature, may be employed.

Subject phosphorus-containing compounds exhibiting reverse thermal gelation may be used to deliver a therapeutic agent. The mixture of a subject phosphorus-containing compound exhibiting reverse thermal gelation and a therapeutic agent, as well as optionally other material(s), may be prepared as solution of the compound below the gelation temperature, often an aqueous solution although any biocompatible solvent may be used, to form a drug delivery liquid exhibiting reverse thermal gelation in which the therapeutic agent or other material(s) may be either partially or completely dissolved. When the therapeutic agent is partially dissolved, or when the therapeutic agent is essentially insoluble, the therapeutic agent may exist in a colloidal state such as a suspension or emulsion. Such drug delivery liquid may then be administered to a patient by a variety of means described herein, whereupon if the body temperature is above the gelation temperature observed for the mixture, the liquid will undergo a reversible thermal gelation to form a depot.

As for subject compositions that do not exhibit reverse thermal gelation, a variety of loading levels of therapeutic agents are contemplated for those compositions that have such a property. The loading level in this instance is most readily measured in comparison to the subject phosphorus-containing compound as opposed to the mixture which may contain a large amount of solvent. In those embodiments in which reverse thermal gelation is desired, the only limitation on loading is one of functionality, namely, the therapeutic agent load may be increased until the thermal gelation properties of the resulting mixture are adversely affected to an unacceptable degree, either in formation of the depot, or ease of administration or otherwise. Although a range of loading levels as broad as those contemplated for subject compositions without reverse thermal gelation are intended, it is anticipated that in most instances when reverse thermal gelation is desired, the loading level will be between about 1 to about 20% by weight, alternatively, about 5, 10, or 15% of therapeutic agent (or agents) to the subject phosphorus-contaning compound.

In certain situations, a drug delivery liquid exhibiting reverse thermal gelation may be administered in the gel state instead of as a solution or liquid mixture. The gelation may be the result of a number of modifications to the drug delivery liquid, such as raising the temperature of the drug delivery liquid to above its gelation temperature prior to administration, or raising the concentration of the subject phosphorus-containing compound exhibiting gelation behavior in the solution to above its saturation concentration at the temperature of administration, or by adding additives to the solution which causes the solution to gel. In any case, the gel thus formed may be administered by the various means disclosed herein or otherwise known to one of skill in the art.

H. Formulations, Dosages for Subject Compositions and Drug Delivery Devices

The subject compositions may be administered by various means, depending on their intended use, as is well known in the art. For example, such compositions may be administered as injections (e.g., intravenous, intramuscular or subcutaneous). Alternatively, the subject compositions may be administered in any of the following fashions: parenteral, ocular, topical, inhalation, transdermal, vaginal, transurethral, rectal, nasal, oral, pulmonary or aural delivery. The mode of administration will in all likelihood depend on whether the subject composition forms a gel due to reverse thermal gelation properties.

Formulations of the subject compositions may be prepared by conventional means known to those of skill in art.

The invention further provides kits for use in treating a disease or condition. For example, the kit may comprise a subject phosphorus-containing compound and a therapeutic agent, either already combined or provided separately. The composition may be packaged in a suitable container. The kit may further comprise instructional materials for using the kit.

In certain embodiments, the subject phosphorus-containing compound will incorporate the therapeutic agent to be delivered in an amount sufficient to deliver to a patient a therapeutically effective amount of the incorporated agent as part of a prophylactic or therapeutic treatment. The desired concentration of therapeutic agent will depend on absorption, inactivation, and excretion rates of the agent as well as the delivery rate of the agent from the composition. It is to be noted that dosage values may also vary with the severity of the condition to be alleviated. Further, dosage will vary depending on the symptoms, age and body weight of the patient, the nature and severity of the disorder to be treated or prevented, the route of administration, and the form of the composition used. Any of the subject compositions may be administered in a single dose or in divided doses. It is to be further understood that for any particular subject, specific dosage regimens should be adjusted over time according to the individual need and the professional judgment of the person administering or supervising the administration of the compositions. Typically, dosing will be determined using techniques known to one skilled in the art.

The use of more than one therapeutic agents in a subject composition may reduce the required dosage for any individual agent because the onset and duration of effect of the different components may be complimentary. In such combined therapy, the different active agents may be delivered together or separately, and simultaneously or at different times within the day.

Toxicity and therapeutic efficacy of subject compositions may be determined by standard pharmaceutical procedures in cell cultures or experimental animals, e.g., for determining the $LD_{50}$ and the $ED_{50}$. Compositions that exhibit large therapeutic indices are preferred. Although compounds that exhibit toxic side effects may be used, care should be taken to design a delivery system that targets the compounds to the desired site in order to reduce side effects.

In another aspect, the present invention is directed to methods of using the subject compositions in medical compositions. In one embodiment, the subject compositions are used for implantation, injection, or otherwise placed totally or partially within the body. In another embodiment, the subject compositions are designed for implantation or injection into the body of an animal. The compositions may also be used to help adhere tissue to tissue or adhere other implants to tissue by virtue of the mechanical bonding or encapsulation of tissue and the compositions.

In another aspect of the invention, the efficacy of treatment using the subject compositions may be compared to treatment regimens known in the art in which the therapeutic agent in question is not encapsulated within a subject phosphorus-containing compound or other treatment regimens. The metrics by which such comparison may be made include survival rates, life expectancy, size of a tumor or neoplasm, rate of growth of a tumor or neoplasm, number of infections, and other metrics known to those of skill in the art and appropriate to the disease or condition being treated. In certain embodiments, the improvement observed for any of such metrics upon treatment with a subject composition as compared to treatment with the same active agent in the such composition absent the subject polymer in such composition may be about 25%, 50% 75%, 100% as effective, or 2, 2, 5, 10, 20, 50, 100, 250 or more times as effective.

In certain embodiments, a solid articles made of, at least in part, a subject composition may be used as a drug delivery device or other medical device. In certain embodiments, the subject composition contains a therapeutic agent. As a structural medical device, the subject compositions of the inventions provide a wide variety of physical forms having specific chemical, physical and mechanical properties suitable for insertion into an anatomic area. Subject compositions may formed into articles of almost any size or shape desired, for example, implantable solid discs or wafers or injectable rods, microspheres, or other microparticles. Typical medical articles also include such as implants as laminates for degradable fabric or coatings to be placed on other implant devices. When a subject composition is flexible or flowable, it may be placed in an anatomic area. It may be inserted into the anatomic area either through an open surgical wound, under direct or indirect vision, or through any of the access devices routinely used in the art to enter such areas, for example, indwelling or acutely-inserted catheters, needles, drains, superselective angiography means and the like.

EXEMPLIFICATIONS

Because of the complexity of the possible formulations, a system of nomenclature for the subject phosphorus-containing compounds has been instituted for clarity, simplicity, and convenience. The designation or name of the formulation will be based upon the following scheme:

ratio of monomers used in the polymeric chain precursor_copolymer name_(initiator)_theoretical Mn of polymeric chain precursor_phosphorus monomer For example, a compound prepared from a polymeric chain precursor made from equimolar amounts of DL-lactide ("DL") and caprolactone ("Cl"), initiated with propylene glycol ("PG") with a theoretical Mn of 2000 Da, and condensed onto ethyl dichlorophosphate, $EOPCl_2$, ("EOP") will be designated "50/50 DL-PLCl (PG) 2000 EOP". A subject phosphorus-containing compound prepared from a polymeric chain precursor made from DL-lactide, initiated with methoxy-capped poly(ethylene glycol) MW=200 ("MPEG 200"), with a theoretical Mn of 1500 Da, and condensed onto $EOPCl_2$ will be designated "100 DL-PL (MPEG 200) 1500 EOP".

The following table lists the names of some of exemplary embodiments of the subject phosphorus-containing compounds of this invention as well as the subunit compositions of their R1 chains. A generic formula for the R1 chain is presented below before the table:

$$* \left[ \left( O - M_1 \right)_{t_1}^{t_2} \left( O - M_2 \right)_{n_2}^{O} \right]_x R_7$$

| Abbreviation | M1 | M2 | R7 | $n_1:n_2$* | X* |
|---|---|---|---|---|---|
| 50/50 DL-PLCl (DD) 500 | $CH(CH_3)CO_2CH(CH_3)$ (L or D) | $(CH_2)_5$ | $O-(CH_2)_{11}CH_3$ | 1:1 | 1 |
| 60/40 DL-PG (DD) 500 | $CH(CH_3)CO_2CH(CH_3)$ (L or D) | $CH_2CO_2CH_2$ | $O-(CH_2)_{11}CH_3$ | 2.4:1.6 | 1 |
| 60/40 DL-PG (MPEG) 500 | $CH(CH_3)CO_2CH(CH_3)$ (L or D) | $CH_2CO_2CH_2$ | $O-(CH_2)_{11}CH_3$ | 2.4:1.6 | 1 |
| 100 PTMC (DD) 500 | $(CH_2)_3O$ | N/A | $O-(CH_2)_{11}CH_3$ | N/A | 5 |

*for the numerical values provided for $n_1$, $n_2$ and x (other than one), an average value is provided for all polymeric chains based on the theoretical determination from the molar ratios used to prepare the polymeric chain precursor.

Example 1

Synthesis of 50/50 DL-PLCl (DD) 500 EOP and 50/50 DL-PLCl (DD) 500 PO

Two low MW, low viscosity, subject phosphorus-containing compounds, denoted 50/50 DL-PLCl (DD) 500 EOP and 50/50 DL-PLCl (DD) 500 PO were prepared by condensation (or coupling) of a polymeric chain precursor onto either ethyl dichlorophosphate, $EOPCl_2$ (for two polymeric chains) or phosphorus oxychloride, $POCl_3$ (for three polymeric chains).

The structure of the polymeric chain precursor, R1, used to prepare these particular subject phosphorus-containing compounds is shown below:

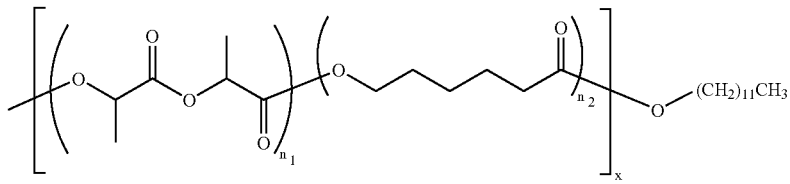

wherein, the average n1 and n2 is approximately two and x is 1, so that the theoretical Mn for the polymeric chain precursor is 702 g/mol.

The polymeric chain precursor in each case was prepared from a 49/51 molar ratio of DL-lactide and caprolactone, targeting a 50/50 ratio in the final polymeric chain precursor, and initiated with 1-dodecanol such that the theoretical ratio of DL-lactide to caprolactone to 1-dodecanol was 2/2/1 and the theoretical Mn was about 700 daltons. The polymerization was conducted for 6 hours at 135° C. using 500 ppm (based on grams of total monomer) tin octoate (SnOct) as the catalyst. The residual monomer was removed from the polymeric chain precursor by vacuum stripping for one hour at 105° C. The polymeric chain precursor was then dissolved in chloroform for reaction with the appropriate phosphohalogenate.

The subject compound 50/50 DL-PLCl (DD) 500 EOP was prepared from the polymeric chain precursor and EOPCl$_2$ (0.50 equivalents relative to 1-dodecanol) using triethylamine (TEA, 2.50 equivalents relative to 1-dodecanol) and 4-dimethylaminopyridine (DMAP, 0.50 equivalents relative to 1-dodecanol) in chloroform solution at −5° C. The EOPCl$_2$ was added to the polymeric chain precursor solution over a period of 30 minutes and the reaction was allowed to proceed for one hour thereafter. Following the reaction, the residual amine contaminants were removed by treatment with ion exchange resins (IERs). The IERs were removed by vacuum filtration and the solvent was removed under vacuum. The yield of the neat liquid was 107 grams (150 g theoretical yield, 71%) for the first batch, and 26 g (45 g theoretical yield, 59%) for the second batch.

The subject compound 50/50 DL-PLCl (DD) 500 PO was prepared by a condensation process identical to the one used to produce the previous compound, except that phosphorus oxychloride (POCl$_3$, 0.33 equivalents relative to 1-dodecanol) was substituted for the EOPCl$_2$ in the process. The yield of the neat liquid was 90 grams (144 g theoretical yield, 63%) for a first batch, and 25 grams (43 g theoretical yield, 58%) for a second batch. Both of the 50/50 Dl-PLCl (DD) 500 phosphorus compounds are slightly hazy, faintly yellow liquids at room temperature.

Example 2

Molecular Weight (MW) Data for 50/50 DL-PLCl (DD) 500 EOP and 50/50 DL-PLCl (DD) 500 PO Table I shows the MW data obtained for the 50/50 Dl-PLCl (DD) 500 EOP and 50/50 DL-PLCl (DD) 500 PO and their theoretical values of Mn. The values for Mn, Mw, and MWD (w/Mn) were determined by GPC using a differential refractive index detector, one 500 and one 50 Polymer Labs PLgel® column in series and a polystyrene calibration curve. Values of Mn were also determined by $^1$H NMR. The Mns determined by $^1$H NMR agree well with the theoretical values whereas the Mns determined by GPC are somewhat higher. The values are determined using a calibration curve generated from polystyrene standards. The Mws determined by GPC for these subject phosphorus-containing compounds are reasonable and the MWDs are low as expected for products of a coupling process. The data for the two batches of 50/50 DL-PLCl (DD) 500 EOP agree very well with one another as do the data for the two batches of 50/50 DL-PLCl (DD) 500 PO.

TABLE I

Molecular Weight Data for 50/50 DL-PLCl (DD) 500 Compounds

| Formulation | Theor. Mn, Da | Mn, Da (NMR) | Mn, Da (GPC) | Mw, Da (GPC) | MWD (Mw/Mn) |
|---|---|---|---|---|---|
| 50/50 DL-PLCl (DD) 500 EOP batch A121-72 | 1496 | 1400 | 2300 | 3100 | 1.26 |
| 50/50 DL-PLCl (DD) 500 EOP batch A124-57 | 1496 | 1400 | 2300 | 2900 | 1.27 |
| 50/50 DL-PLCl (DD) 500 PO batch A121-74 | 2153 | 1900 | 3000 | 3700 | 1.23 |
| 50/50 DL-PLCl (DD) 500 PO batch A124-48 | 2153 | 2000 | 3100 | 3800 | 1.23 |

Table II shows the composition data obtained for 50/50 DL-PLCl (DD) 500 EOP and 50/50 DL-PLCl (DD) 500 PO determined by $^1$H NMR. The ratios of D-lactide to caprolactone determined by $^1$H NMR are 51/49 for one batch of each of 50/50 DL-PLCl (DD) 500 EOP and 50/50 DL-PLCl (DD) 500 PO, and 49/51 and 52/48 for the other batch of 50/50 DL-PLCl (DD) 500 EOP and 50/50 DL-PLCl (DD) 500 PO, respectively, close to the targeted ratio of 50/50. The ratios of DL-lactide to caprolactone to 1-dodecanol were also determined by $^1$H NMR and yielded actual values that are very close to the theoretical ratio of 2/2/1 for each such compound.

TABLE II

Composition Data for 50/50 DL-PLCl (DD) 500 Compounds

| Sample | Mole % DL-lactide | Mole % Caprolactone | Ratio, DL-lactide/Caprolactone/1-dodecanol |
|---|---|---|---|
| 50/50 DL-PLCl (DD) 500 EOP - Batch One | 51 | 49 | 1.8/1.8/1.0 |
| 50/50 DL-PLCl (DD) 500 EOP - Batch Two | 49 | 51 | 1.8/1.8/1.0 |
| 50/50 DL-PLCl (DD) 500 PO - Batch One | 51 | 49 | 1.7/1.6/1 |
| 50/50 DL-PLCl (DD) 500 PO - Batch Two | 52 | 48 | 1.9/1.8/1.0 |
| Theoretical | 50 | 50 | 2.0/2.0/1.0 |

Example 3

Synthesis of 60/40 DL-PLG (DD) 500 Compounds

A second group of subject compounds were prepared using the synthetic approach as discussed in Example 1, denoted 60/40 DL-PLG (DD) 500 EOP and 60/40 DL-PLG (DD) 500 PO. The structure of the polymeric chain precursor, R1, used to prepare these subject phosphorus-containing compounds is shown below:

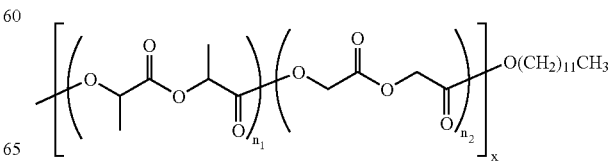

wherein, the average n1 and n2 is approximately 2.4 and 1.6, respectively, and x is 1, so that the theoretical Mn for the polymeric chain precursor is 718 g/mol.

The polymeric chain precursor in each case was prepared from a 60/40 molar ratio of DL-lactide and glycolide, targeting an approximately 60/40 ratio in the final polymeric chain precursor, and initiated with 1-dodecanol such that the theoretical ratio of DL-lactide to glycolide to 1-dodecanol was 2.4/1.6/1.0 and the theoretical Mn was about 700 daltons. The polymerization was conducted for 3 hours at 155° C. using 200 ppm (based on grams of total monomer) of SnOct as the catalyst. The residual monomer was removed from the polymeric chain precursor by vacuum stripping for one hour at 105° C. The polymeric chain precursor was then dissolved in chloroform for reaction with the appropriate phosphohalogenate.

The subject compound 60/40 DL-PLG (DD) 500 EOP was prepared from the polymeric chain precursor and EOPCl$_2$ (0.50 equivalents relative to 1-dodecanol) using TEA (2.50 equivalents relative to 1-dodecanol) and DMAP (0.50 equivalents relative to 1-dodecanol) in chloroform solution at –5° C. The EOPCl$_2$ was added to the polymeric chain precursor solution over a period of 30 minutes and the reaction was allowed to proceed for one hour thereafter. Following the reaction the residual amine contaminants were removed by treatment with IERs as detailed above. The IERs were removed by vacuum filtration and the solvent was removed under vacuum. The yields of the neat liquid, 60/40 DL-PLG (DD) 500 EOP, were 26 grams (43 g theoretical yield, 60%) for one batch and 84 grams (143 g theoretical yield, 59%) for a second batch.

The subject compound 60/40 DL-PLG (DD) 500 PO was prepared by an identical process identical except that POCl$_3$ (0.33 equivalents relative to 1-dodecanol) was substituted for the EOPCl$_2$ in the process. The yield of the neat liquid 60/40 DL-PLG (DD) 500 PO, was 18 grams (41 g theoretical yield, 60%) for batch one and 91 grams (138 g theoretical yield, 66%) for batch two. Both the 60/40 DL-PLG (DD) 500 compounds are slightly hazy, faintly yellow liquids at room temperature.

Example 4

MW Data for 60/40 DL-PLG (DD) 500

Table III shows the MW data obtained for the 60/40 DL-DLG (DD) 500 EOP and 60/40 DL-PLG (DD) 500 PO compounds described above and their theoretical values of Mn. The values for Mn, Mw, and MWD (Mw/Mn) were determined by GPC using a differential refractive index detector, one 500 and one 50 Polymer Labs PLgel® column in series and a polystyrene calibration curve. Values of Mn were also determined by $^1$H NMR. The Mns determined by $^1$H NMR agree well with the theoretical values whereas the Mns determined by GPC for these subject phosphorus-containing compounds are reasonable and the MWDs are low, as expected for products of a coupling process. The data for the two batches of 60/40 DL-PLG (DD) 500 EOP agree very well with one another as do the data for the two batches of 60/40 DL-PLG (DD) 500 PO.

TABLE III

Molecular Weight Data for 60/40 DL-PLG (DD) 500 Compounds

| Formulation | Theor. Mn, Da | Mn, Da (NMR) | Mn, Da (GPC) | Mw, Da (GPC) | MWD (Mw/Mn) |
|---|---|---|---|---|---|
| 60/40 DL-PLG (DD) 500 EOP - Batch One | 1526 | 1400 | 2300 | 3000 | 1.30 |
| 60/40 DL-PLG (DD) 500 EOP - Batch Two | 1526 | 1400 | 2400 | 3000 | 1.25 |
| 60/40 DL-PLG (DD) 500 PO - Batch One | 2198 | 2000 | 3200 | 4000 | 1.25 |
| 60/40 DL-PLG (DD) 500 PO - Batch Two | 2198 | 2000 | 3100 | 3800 | 1.23 |

Table IV shows the composition data obtained for the 60/40 DL-PLG (DD) 500 EOP and 60/40 DL-PLG (DD) 500 PO compounds determined by $^1$H NMR. The ratios of DL-lactide to glycolide determined by $^1$H NMR are 57/43 for both batches of 60/40 DL-PLG (DD) 500 EOP and 55/45 and 58/42 for the two batches of 60/40 DL-PLG (DD) 500 PO, close to the targeted ratio of 60/40. The ratio of DL-lactide to glycolide to 1-dodecanol were also determined by $^1$H NMR and yielded actual values that are close to the theoretical ratio of 2.4/1.6/1.0.

TABLE IV

Composition Data 60/40 DL-PLG (DD) 500 Compounds

| Sample | Mole % DL-lactide | Mole % Caprolactone | Ratio, DL-lactide/ Caprolactone/1-dodecanol |
|---|---|---|---|
| 60/40 DL-PLG (DD) 500 EOP - Batch One | 57 | 43 | 2.0/1.5/1.0 |
| 60/40 DL-PLG (DD) 500 EOP - Batch Two | 57 | 43 | 2.0/1.5/1.0 |
| 60/40 DL-PLG (DD) 500 PO - Batch One | 55 | 45 | 1.9/1.6/1.0 |
| 60/40 DL-PLG (DD) 500 PO - Batch Two | 58 | 42 | 2.1/1.5/1.0 |
| Theoretical | 60 | 40 | 2.4/1.6/1.0 |

Example 5

Synthesis of 100 PTMC (DD) 500 Compounds

Subject phosphorus-containing compounds, denoted 100 PTMC (DD) 500 EOP and 100 PTMC (DD) 500 PO were prepared using the same synthetic strategy as discussed in the preceding examples:

The structure of the polymeric chain precursor, R1, used to prepare the subject compounds is shown below.

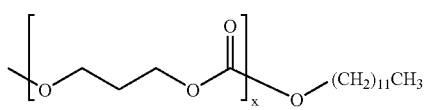

wherein x is 5 and the theoretical Mn for the polymeric chain precursor is 697 g/mol.

The polymeric chain precursor in each case was prepared from trimethylene carbonate (TMC) initiated with 1-dodecanol such that the theoretical ratio of TMC was 5/1 and the theoretical Mn was about 700 daltons. The polymerization was conducted for 3 hours at 155° C. using 300 ppm (based on grams of total monomer) of SnOct as the catalyst. The residual monomer was removed from the polymeric chain precursor by vacuum stripping for one hour at 105° C. The polymeric chain precursor was then dissolved in chloroform for reaction with the appropriate phoshohalogenate.

The subject compound 100 PTMC (DD) 500 EOP was prepared from the polymeric chain precursor and EOPCl$_2$ (0.50 equivalents relative to 1-dodecanol) using TEA (2.50 equivalents relative to 1-dodecanol) and DMAP (0.50 equivalents relative to 1-dodecanol) in chloroform solution at −5° C. The EOPCl$_2$ was added to the polymeric chain precursor solution over a period of 30 minutes and the reaction was allowed to proceed for one hour thereafter. Following the reaction the residual amine contaminants were removed by treatment with IERs as detailed above. The IERs were removed by vacuum filtration and the solvent was removed under vacuum. The yields of the neat liquid 100 PTMC (DD) EOP was 20 grams (44 g theoretical yield, 45%) for one batch and 86 grams (148 g theoretical yield, 58%) for a second batch.

The subject compound 100 PTMC (DD) 500 PO was prepared by an identical process, except that POCl$_3$ (0.33 equivalents relative to 1-dodecanol) was substituted for the EOPCl$_2$ in the process. The yields of the neat liquid 100 PTMC (DD) PO was 27 grams (43 g theoretical yield, 63%) for one batch and 80 grams (142 g theoretical yield, 56%) for a second batch. Both the 100 PTMC (DD) 500 subject phosphorus-containing compounds are slightly hazy, faintly yellow liquids at room temperature.

Example 6

MW Data for 100 PTMC (DD) 500 Compounds

Table V shows the MW data obtained for 100 PTMC (DD) 500 EOP and 100 PTMC (DD) 500 PO and their theoretical values of Mn. The values for Mn, Mw, and MWD (Mw/Mn) were determined by GPC using a differential refractive index detector, one 500 and one 50 Polymer Labs PLgel® column in series and a polystyrene calibration curve. Values of Mn were also determined by $^1$H NMR. The Mns determined by $^1$H NMR agree well with the theoretical values whereas the Mns determined by GPC using are somewhat higher. This is not surprising since the values are determined using a calibration curve generated from polystyrene standards. However, the Mws and MWDs for these formulations are larger than expected.

TABLE V

Molecular Weight Data for 100 PTMC (DD) 500 Compounds

| Formulation | Theor. Mn, Da | Mn, Da (NMR) | Mn, Da (GPC) | Mw, Da (GPC) | MWD (Mw/Mn) |
| --- | --- | --- | --- | --- | --- |
| 100 PTMC (DD) 500 EOP - Batch One | 1483 | 1400 | 2600 | 3500 | 1.35 |
| 100 PTMC (DD) 500 EOP - Batch Two | 1483 | 1400 | 2500 | 4500 | 1.80 |
| 100 PTMC (DD) 500 PO - Batch One | 2134 | 2000 | 2900 | 6800 | 2.34 |
| 100 PTMC (DD) 500 PO - Batch Two | 2134 | 1900 | 2700 | 5800 | 2.15 |

The values of Mw measured by GPC for the 50/50 DL-PLCl (DD) EOP polymer described in Example 1 and the 60/40 DL-PLG (DD) EOP polymer described in Example 2 were approximately 3000 Da in each case, whereas the values of Mw measured by GPC for the 100 PTMC (DD) 500 EOP compound were somewhat higher, 3500 Da and 4500 Da for the two batches. The values of Mn measured by GPC for each of these compositions are not significantly different. This results in much broader MWDs, defined as Mw/Mn, for the 100 PTMC (DD) 500 EOPs. An examination of the chromatograms for each type of formulation clearly illustrates this observation. FIG. 1 shows the overlaid chromatograms for three phosphorus compounds with two polymeric chains: 50/50 DL-PLCl (DD) 500 EOP, 60/40 DL-PLG (DD) 500 EOP, and 100 PTMC (DD) 500 EOP. Clearly, the MWD for 100 PTMC (DD) 500 EOP exhibits a distinct high-MW shoulder and a jagged low-MW tail indicative of oligomers partially separated by the GPC columns.

A similar analysis of the data for the various compounds with three polymeric chains lead to similar conclusions. The values of MW measured by GPC for the 50/50 DL-PLCl (DD) PO compound described in Example 1 and the 60/40 DL-PLG (DD) PO compound described in Example 2 were approximately 4000 Da in each case, whereas the values of MW measured by GPC for the 100 PTMC (DD) 500 PO compounds were somewhat higher, 6800 Da and 5800 Da. Again, the values of Mu measured by GPC for each of these compounds are not significantly different resulting in much broader MWDs for the 100 PTMC (DD) 500 PO compounds. FIG. 2 shows the overlaid chromatograms for three compounds: 50/50 DL-PLCl (DD) 500 PO, 60/40 DL-PLG (DD) 500 PO and 100 PTMC (DD) 500 PO. Clearly, the MWD for 100 PTMC (DD) 500 PO is much broader than the MWDs of the other two formulations whose chromatograms are almost superimposable. The chromatogram for 100 PTMC (DD) 500 PO exhibits a bimodal MWD, having a high MW component that is not present in the other two compounds and a jagged low MW tail indicative of oligomers partially separated by the GPC columns.

Table VI shows the ratios of TMC to 1-dodecanol for the 100 PTMC (DD) EOPS and 100 PTMC (DD) POs determined by $^1$H NMR. The actual ratios are close to the theoretical ratio of 5 to 1, ranging from 4.3 to 4.7.

TABLE VI

Composition Data for 100 PTMC (DD) EOP and 100 PTMC (DD) PO Compounds

| Sample | Ratio, TMC/1-dodecanol |
| --- | --- |
| 100 PTMC (DD) EOP - Batch One | 4.4 |
| 100 PTMC (DD) EOP - Batch Two | 4.4 |
| 100 PTMC (DD) PO - Batch One | 4.7 |
| 100 PTMC (DD) PO - Batch Two | 4.3 |
| Theoretical | 5.0 |

Example 7

Synthesis of Subject Compounds Using MPEG 355 as the Polymeric Chain Precursor Initiator Four subject phosphorus-containing compounds incorporating MPEG 355 were synthesized using the synthetic strategy described in the preceding examples: 60/40 DL-PLG (MPEG 355) 500 EOP, 60/40 DL-PLG (MPEG 355) 1000 EOP, 60/40 DL-PLG (MPEG 355) 500 PO, and 60/40 DL-PLG (MPEG 355) 1000 PO.

The 60/40 DL-PLG (MPEG 355) 500 polymeric chain precursors were prepared from 19.52 g (0.135 mole) of DL-lactide, 10.48 g of glycolide (0.090 mole), and 21.30 g (0.060 mole) of MPEG 355 as the initiator. The components above were transferred in a 250 mL 3-neck round bottom flask equipped with a gas joint connected to a dry argon gas source, a stirrer bearing/shaft/paddle assembly, and a glass stopper and mixed at 150° C. in an oil bath. When the reaction mixture became homogeneous, 115 L of a solution of tin octoate (SnOct) in toluene (1.3041 g of SnOct in 10 mL of anhydrous toluene), equivalent to 0.05% w/w SnOct, were added to the melt. The polymerization was allowed to proceed for 5 hours at 150° C. at which time the oil bath temperature was reduced to 105° C. The residual monomer was removed under vacuum at 105° C. for 1 hour and then the flask was removed from the oil bath, allowed to cool to room temperature under argon gas, and allowed to stand over night under argon gas.

The 60/40 DL-PLG (MPEG 355) 1000 polymeric chain precursors were prepared from 19.52 g (0.135 mole) of DL-lactide, 10.48 g of glycolide (0.090 mole), and 10.65 g (0.030 mole) of MPEG 355 as the initiator. The components above were transferred in a 250 mL 3-neck round bottom flask equipped with a gas joint connected to a dry argon gas source, a stirrer bearing/shaft/paddle assembly, and a glass stopper and mixed at 150° C. in an oil bath. When the reaction mixture became homogeneous, 115 L of a solution of tin octoate (SnOct) in toluene (1.3071 g of SnOct in 10 mL of anhydrous toluene), equivalent to 0.05% w/w SnOct, were added to the melt. The polymerization was allowed to proceed for 5 hours at 150° C. at which time the oil bath temperature was reduced to 105° C. The residual monomer was removed under vacuum at 105° C. for 1 hour and then the flask was removed from the oil bath, allowed to cool to room temperature under argon gas, and allowed to stand over night under argon gas.

The subject compounds 60/40 DL-PLG (MPEG 355) 500 EOP and 60/40 DL-PLG (MPEG 355) 1000 EOP, were prepared from a polymeric chain precursor and EOPCl$_2$ (0.50 equivalents relative to MPEG 355 used in the polymeric chain precursor) using triethylamine (TEA, 2.5 equivalents relative to MPEG 355) and 4-dimethylaminopyridine (DMAP, 0.5 equivalents relative to MPEG) in chloroform solution at −5° C. The EOPCl$_2$ was added to the polymeric chain precursor solution over a period of 30 minutes and the reaction was allowed to proceed for one hour thereafter. Following the reaction the residual amine contaminants were removed by treatment with IER (112.5 g of Dowex® DR-2030 and 90 g of Dowex M-43®). The IERs were removed by vacuum filtration and the solvent was removed under vacuum to yield the neat liquid subject phosphorus-containing compound.

The subject compounds 60/40 DL-PLG (MPEG 355) 500 PO and 60/40 DL-PLG (MPEG 355) 1000 PO were prepared by an identical process, except that POCl$_3$ (0.33 equivalents relative to MPEG 355) was substituted for the EOPCl$_2$ in the process and 56 g of Dowex® DR-2030 and 45 g of Dowex M-43® were used in the IER treatment rather than the amounts listed above.

Example 8

MW Data for Subject Compounds Using MPEG 355 as the Polymeric Chain Precursor Initiator Table VII shows the MW data obtained for the subject compounds incorporating MPEG 355 and their theoretical values of Mn. The Mns determined by $^1$H NMR agree well with the theoretical values whereas the Mns determined by GPC are somewhat higher. This is not surprising since the compounds are low MW and the values are determined using a calibration curve generated from polystyrene standards. The Mws determined by GPC for these compounds are reasonable and the MWDs are low, about 1.2 to 1.4.

TABLE VII

MW data for 60/40 DL-PLG (MPEG 355) Compounds

| Formulation | Theor. Mn, Da | Mn, Da (NMR) | Mn, Da (GPC) | Mw, Da (GPC) | MWD (Mw/Mn) |
|---|---|---|---|---|---|
| 60/40 DL-PLG (MPEG 355) 500 EOP - Batch One | 1812 | 1698 | 2600 | 3200 | 1.23 |
| 60/40 DL-PLG (MPEG 355) 500 EOP - Batch Two | 1812 | 1612 | 2600 | 3300 | 1.27 |
| 60/40 DL-PLG (MPEG 355) 500 PO - Batch One | 2627 | 2498 | 3100 | 4100 | 1.32 |
| 60/40 DL-PLG (MPEG 355) 500 PO - Batch Two | 2627 | 2414 | 3200 | 4300 | 1.34 |
| 60/40 DL-PLG (MPEG 355) 1000 EOP | 2800 | 2704 | 3800 | 5200 | 1.37 |
| 60/40 DL-PLG (MPEG 355) 1000 PO | 4110 | 3886 | 5000 | 7200 | 1.44 |

Table VIII below shows the composition data obtained for the 60/40 DL-PLG (MPEG 355) 500 EOP and 60/40 DL-PLG (MPEG 355) 500 PO compounds and Table IX below shows the composition data obtained for the 60/40 DL-PLG (MPEG 355) 1000 EOP and 60/40 DL-PLG (MPEG 355) 1000 PO compounds. The actual materials prepared are close to the targeted materials in terms of both composition and MW. However, the amount of DL-lactide present in these compounds is slightly lower than the theoretical amount.

TABLE VIII

Composition Data for 60/40 DL-PLG (MPEG 355) 500 EOP and 60/40 DL-PLG (MPEG 355) 500 PO

| Sample | Mole % DL-lactide | Mole % glycolide | Ratio, DL-lactide/ glycolide/1-dodecanol |
|---|---|---|---|
| 60/40 DL-PLG (MPEG 355) 500 EOP - Batch One | 55 | 45 | 1.9:1.5:1.0 |
| 60/40 DL-PLG (MPEG 355) 500 EOP - Batch Two | 52 | 48 | 1.6:1.5:1.0 |
| 60/40 DL-PLG (MPEG 355) 500 PO - Batch One | 57 | 43 | 2.0:1.5:1.0 |
| 60/40 DL-PLG (MPEG 355) 500 PO - Batch Two | 55 | 45 | 1.8:1.5:1.0 |
| Theoretical | 60 | 40 | 2.3:1.5:1.0 |

TABLE IX

Composition Data for 60/40 DL-PLG (MPEG 355) 1000 EOP and 60/40 DL-PLG (MPEG 355) 1000 PO

| Sample | Mole % DL-lactide | Mole % glycolide | Ratio, DL-lactide/ glycolide/1-dodecanol |
|---|---|---|---|
| 60/40 DL-PLG (MPEG 355) 1000 EOP | 57 | 43 | 4.1:3.1:1.0 |
| 60/40 DL-PLG (MPEG 355) 1000 PO | 57 | 43 | 4.0:3.0:1.0 |
| Theoretical | 60 | 40 | 4.5:3.0:1.0 |

Example 9

MW Data for Subject Compounds Using MPEG 550 as the Polymeric Chain Precursor Initiator Two subject phosphorus-containing compounds incorporating MPEG 550 were synthesized using the synthetic strategy described in the preceding examples: 75/25 DL-PLG (MPEG 550) 1000 EOP and 75/25 DL-PLG (MPEG 550) 1000 PO. The general structure of the polymeric chain precursors used to prepare these compounds is shown below:

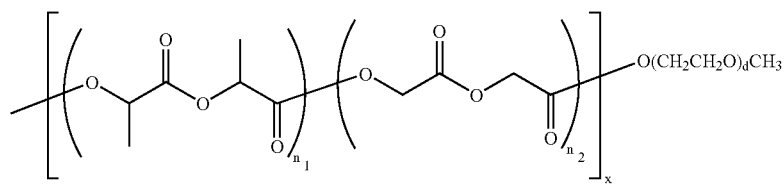

The polymeric chain precursors were prepared from the appropriate monomers using MPEG 550 as the initiator and the subject compounds were prepared from the polymeric chain precursor and either EOPCl$_2$ or phosphorus oxychloride, POCl$_3$.

The 75/25 DL-PLG (MPEG 550) 1000 polymeric chain precursors were prepared from 35.48 g (0.246 mole) of DL-lactide, 9.52 g of glycolide (0.082 mole), and 24.75 g (0.045 mole) of MPEG 550 as the initiator. The components above were transferred to a 500 mL 3 neck round bottom flask equipped with a gas joint connected to a dry argon gas source, a stirrer bearing/shaft/paddle assembly, and a glass stopper and mixed at 150° C. in an oil bath. When the reaction mixture became homogeneous, 172 L of a solution of tin octoate (SnOct) in toluene (1.3071 g of SnOct in 10 mL of anhydrous toluene), equivalent to 0.05% w/w SnOct, were added to the melt. The polymerization was allowed to proceed for 5 hours at 150° C. at which time the oil bath temperature was reduced to 105° C. The residual monomer was removed under vacuum at 105° C. for 1 hour and then the flask was removed from the oil bath, allowed to cool to room temperature under argon gas, and allowed to stand overnight under argon gas.

75/25 DL-PLG (MPEG 550) 1000 EOP was prepared from a polymeric chain precursor and EOPCl$_2$ (0.50 equivalents relative to MPEG 550 used in the polymeric chain precursor) using triethylamine (TEA, 2.5 equivalents relative to MPEG 550) and 4-dimethylaminopyridine (DMAP, 0.5 equivalents relative to MPEG) in chloroform solution at −5° C. The EOPCl$_2$ was added to the polymeric chain precursor solution over a period of 30 minutes and the reaction was allowed to proceed for one hour thereafter. Following the reaction the residual amine contaminants were removed by treatment with ion exchange resins (IERs) (84 g of Dowex® DR-2030 and 68 g of Dowex M-43®). The IERs were removed by vacuum filtration and the solvent was removed under vacuum to yield the neat liquid PPE. 75/25 DL-PLG (MPEG 550) 1000 PO was prepared by an identical process, except that phosphorus oxychloride (POCl$_3$, 0.33 equivalents relative to MPEG 550) was substituted for the EOPCl$_2$ in the process.

Table X shows the MW data obtained for 75/25 DL-PLG (MPEG 550) 1000 EOP and 75/25 DL-PLG (MPEG 550) 1000 PO compounds and their theoretical values of Mn. The Mns determined by $^1$H NMR agree well with the theoretical values whereas the Mns determined by GPC are somewhat higher. This is not surprising since the polymers are low MW and the values are determined using a calibration curve generated from polystyrene standards. The Mws determined by GPC are reasonable and the MWDs are low, about 1.4 to 1.5.

Table XI below shows the composition data obtained for 75/25 DL-PLG (MPEG 550) 1000 EOP and 75/25 DL-PLG (MPEG 550) 1000 PO compounds. The actual materials prepared are close to the targeted materials in terms of both composition and MW.

Table XII below shows the composition of the 75/25 DL-PLG (MPEG 550) 1000 EOP and 75/25 DL-PLG (MPEG 550) 1000 PO expressed in terms of the weight percent (% w/w) of polyester, MPEG, and phosphorus (P).

Table XIII below shows the gel-point temperatures measured for 75/25 DL-PLG (MPEG 550) 1000 EOP and 75/25 DL-PLG (KEG 550) 1000 PO using a concentration of 35% (w/w) in deionized water. Below the gel-point temperature the samples were viscous but fluid. At the gel-point the samples were very viscous, resistant to flow, and had become slightly opaque. Above the gel-point temperature the samples became completely opaque, then precipitated. These observations were made by visual inspection upon heating the samples.

TABLE X

MW data for 75/25 DL-PLG (MPEG 550) 1000 EOP and 75/25 DL-PLG (MPEG 550) 1000 PO

| Sample & Description | Theoretical Mn, Da | Mn, Da ($^1$H NMR) | Mn, Da (GPC/CC) | Mw, Da (GPC/CC) | MWD (Mw/Mn) |
|---|---|---|---|---|---|
| 75/25 DL-PLG (MPEG 550) 1000 EOP | 3150 | 3108 | 3900 | 5300 | 1.36 |
| 75/25 DL-PLG (MPEG 550) 1000 PO | 4634 | 4772 | 5100 | 7700 | 1.51 |

TABLE XI

Composition Data for 75/25 DL-PLG (MPEG 550) 1000 EOP and 75/25 DL-PLG (MPEG 550) 1000 PO

| Sample | Mole % DL-lactide | Mole % glycolide | Ratio, DL-lactide/glycolide/MPEG |
|---|---|---|---|
| 75/25 DL-PLG (MPEG 550) 1000 EOP | 75 | 25 | 4.8/1.6/1.0 |
| 75/25 DL-PLG (MPEG 550) 1000 PO | 74 | 26 | 5.1/1.8/1.0 |
| Theoretical | 75 | 25 | 5.5/1.8/1.0 |

TABLE XII

Composition Data (% w/w) for 75/25 DL-PLG (MPEG 550)
1000 EOP and 75/25 DL-PLG (MPEG 550) 1000 PO

| Sample | % (w/w) Polyester[a] | % (w/w) MPEG[a] | % (w/w) P |
|---|---|---|---|
| 75/25 DL-PLG (MPEG 550) 1000 EOP | 58 | 42 | 1.0 |
| 75/25 DL-PLG (MPEG 550) 1000 PO | 60 | 40 | 0.7 |

TABLE XIII

Gel-Point Temperatures for 75/25 DL-PLG (MPEG 550)
1000 EOP and 75/25 DL-PLG (MPEG 550) 1000 PO

| Description | Gel-Point Temperature, °C. |
|---|---|
| 75/25 DL-PLG (MPEG 550) 1000 EOP | 47 |
| 75/25 DL-PLG (MPEG 550) 1000 PO | 47 |

In addition to the measurements of gel-point temperature described above, it will be possible to measure gel-point temperatures by other means. One example known in the art is described in Jeong et al., Journal of Controlled Release 62:109-114 (1999). By way of example, a related method will involve preparing a sample of a subject phosphorus-containing polymer in water in the concentration range of 25 to 50% (w/w), alternatively about 35%. About 30 mg of the solution will be placed in an aluminum DSC crucible which will then be hermetically sealed and placed in the sample position in a suitable DSC module. Another aluminum DSC crucible containing the same net weight of water will be hermetically sealed and placed in the reference position in the same DSC module. The module will be cooled to 4 C briefly then heated from 4 C to 70 C at 1 C/min to generate the sample thermogram. A blank thermogram will be generated by running 2 aluminum DSC crucibles in the sample and reference slots of the module containing equal amounts of water. The same heating profile will be used to generate the blank thermogram. Using the DSC software, the data collected from the blank thermogram will be subtracted from the sample thermogram. The resulting thermogram should look similar to the data described in the Jeong et al. reference.

Example 10

Other Subject Phosphorus-Containing Compounds

Using the methods described above, a number of additional subject phosphorus containing compounds were prepared and certain of their properties measured:

TABLE XIV

Other Subject Phosphorus-Containing Compounds

| Formulation | Theoretical Mn, Da | Mn, Da ($^1$H NMR) | Mn, Da (GPC/CC) | Mw, Da (GPC/CC) | MWD (Mw/Mn) |
|---|---|---|---|---|---|
| 75/25 DL-PLG (mPEG 550) 1000 EOP | 3150 | 3108 | 3900 | 5300 | 1.36 |
| 75/25 DL-PLG (mPEG 550) 1000 PO | 4634 | 4772 | 5100 | 7700 | 1.51 |
| 75/25 DL-PLG (mPEG 550) 1400 EOP | 4154 | 4152 | 5500 | 8000 | 1.45 |
| 75/25 DL-PLG (mPEG 550) 1400 PO | 6140 | 5804 | 7000 | 10,600 | 1.51 |
| 75/25 DL-PLG (mPEG 550) 1800 EOP | 4954 | 4970 | 5800 | 8700 | 1.50 |
| 75/25 DL-PLG (mPEG 550) 1800 PO | 7340 | 7625 | 6200 | 10,500 | 1.69 |
| 75/25 DL-PLG (mPEG 350) 630 EOP | 1912 | 1535 | 2100 | 2600 | 1.24 |
| 75/25 DL-PLG (mPEG 350) 630 EOP | 1912 | 1898 | 2900 | 3900 | 1.34 |
| 75/25 DL-PLG (mPEG 350) 630 PO | 2915 | 2741 | 4300 | 5400 | 1.26 |
| 100 DL-PL (mPEG 550) 1400 EOP | 3994 | 3943 | 5700 | 7400 | 1.30 |
| 100 L-PL (mPEG 550) 1400 EOP | 3994 | 3860 | 3200 | 3700 | 1.16 |

TABLE XV

Other Subject Phosphorus-Containing Compounds Continued
The theoretical values are in parenthese following the measured value.

| Formulations | Mole % DL-lactide | Mole % glycolide | Ratio, DL-lactide/glycolide/mPEG |
|---|---|---|---|
| 75/25 DL-PLG (mPEG 550) 1000 EOP | 75 (75) | 25 (25) | 4.8/1.6/1.0 (5.5/1.8/1.0) |
| 75/25 DL-PLG (mPEG 550) 1000 PO | 74 (75) | 26 (25) | 5.1/1.8/1.0 (5.5/1.8/1.0) |
| 75/25 DL-PLG (mPEG 550) 1400 EOP | 74 (75) | 26 (25) | 7.6/2.6/1.0 (7.7/2.6/1.0) |
| 75/25 DL-PLG (mPEG 550) 1400 PO | 74 (75) | 26 (25) | 7.0/2.4/1.0 (7.7/2.6/1.0) |
| 75/25 DL-PLG (mPEG 550) 1800 EOP | 74 (75) | 26 (25) | 9.8/3.4/1.0 (9.9/3.3/1.0) |
| 75/25 DL-PLG (mPEG 550) 1800 PO | 74 (75) | 26 (25) | 10.3/3.5/1.0 (9.9/3.3/1.0) |
| 75/25 DL-PLG (mPEG 350) 630 EOP | 66 (75) | 34 (25) | 1.9/0.8/1.0 (3.5/1.2/1.0) |
| 75/25 DL-PLG (mPEG 350) 630 EOP | 75 (75) | 25 (25) | 3.0/1.0/1.0 (3.5/1.2/1.0) |
| 75/25 DL-PLG (mPEG 350) 630 PO | 74 (75) | 26 (25) | 2.9/1.1/1.0 (3.5/1.2/1.0) |
| 100 DL-PL (mPEG 550) 1400 EOP | 100 (100) | 0 (0) | 9.5/NA/1.0 (9.7/NA/1.0) |
| 100 L-PL (mPEG 550) 1400 EOP | 100 (100) | 0 (0) | 9.2/NA/1.0 (9.7/NA/1.0) |

The 100 L-PL (mPEG 550) 1400 EOP is a solid at room temperature and has a waxy consistency.

Example 11

Preparation of Paste from a Subject Compound and Hydroxylapatite

A subject compound prepared in Example 2, 60/40 DL-PLG (DD) EOP, was mixed with hydroxylapatite (calcium phosphate hydroxide, $3Ca_3(PO_4)2Ca(OH)_2$ to form a paste as follows. Approximately 1.2 g of hydroxylapatite powder was added to approximately 2.6 g of the polymer on a piece of Teflon® film and the two materials were mixed thoroughly to form a uniform paste. The paste was very stiff and tacky, even when wetted with water. This combination of materials may be used to mend bone defects or to provide a continuous matrix when other solid biodegradable implants, such as hydroxyapatite plugs, are inserted into bone gaps.

6. References

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Patents And Patent Applications

U.S. Pat. Nos. 5,747,058, 5,968,542, 6,051,558, 5,278,201, 5,278,202, 5,324,519, 5,340,849, 5,368,859, 5,487,897, 5,599,552, 5,632,727, 5,681,873, 5,702,716, 5,702,717, 5,725,491, 5,733,950, 5,736,152, 5,739,176, 5,744,153, 5,759,563, 5,780,044, 5,792,469, 5,888,533, 5,945,115, 5,962,006, 5,990,194, 6,004,573, 6,120,789, 6,143,314, 5,702,717, 6,117,949, 6,166,173, 6,153,212 and 6,201,072.

Publications

Choi et al., Macromolecules 31:8766-8774 (1998); Ha et al., Journal of Controlled Release 62:381-392 (1999); Jeong et al., Nature 388:860-862 (August 1997); Jeong et al., Colloids and Surfaces B: Biointerfaces 16:185-193 (1999); Jeong et al., Journal of Controlled Release 63:155-163 (2000); Jeong et al., Journal of Controlled Release 62:109-114 (1999); Jeong et al., Macromolecules 32:7064-7069 (1999); Kim et al., Journal of Controlled Release 72:191-202 (2001); Von Recum et al., Journal of Controlled Release 55:121-130 (1998).

7. Equivalents

Those skilled in the art will recognize, or be able to ascertain using no more than routine experimentation, many equivalents to the specific embodiments of the invention described herein. Such equivalents are intended to be encompassed by the following claims.

We claim:

1. A composition, comprising a phosphorus-containing compound with a star structure represented by the following formula:

$$\underset{(R2)_r}{\overset{\overset{Q}{\parallel}}{P}}(R1)_s$$

wherein, independently for each occurrence:

Q represents —O or —N(R3);

r represents 0 or 1, and s represents 3 or 2, such that r+s=3;

R1 represents a polymeric chain;

R2 represents —H, alkyl, cycloalkyl, —O-alkyl, —O-cycloalkyl, cycloalkenyl, —O-cycloalkenyl, aryl, —O-aryl, heterocycle, —O-heterocycle, polycycle, —O-polycycle, or —N(R4)R5;

R3 represents —H, alkyl, aryl, cycloalkyl, cycloalkenyl, heterocycle, or polycycle;

R4 and R5, each independently, represent a hydrogen, an alkyl, an alkenyl, —$(CH_2)_m$—R6, or R4 and R5, taken together with the N atom to which they are attached complete a heterocycle having from 4 to about 8 atoms in the ring structure;

m represents an integer from 0-10; and

R6 represents —H, alkyl, cycloakyl, —O-alkyl, —O-cycloalkyl, cycloalkenyl, —O-cycloalkenyl, aryl, —O-aryl, heterocycle, —O-heterocycle, polycycle or —O-polycycle.

2. The composition of claim 1, wherein R1 is represented by:

$$\text{Formula II}$$

$$*\left[\left(X_1\underset{Q_1}{\overset{\parallel}{M_1}}\right)_{n_1}^{t_1}\left(X_2\underset{t_2}{\overset{Q_2}{M_2}}\right)_{n_2}\cdots\left(X_s\underset{Q_s}{\overset{\parallel}{M_s}}\right)_{n_s}^{t_s}\right]_x R_7$$

wherein

* represents the central phosphorus atom of Formula I;

R7 represents —O-alkyl, —O-cycloalkyl, —O-aryl, —O-heterocyclyl, —S-alkyl, —S-cycloalkyl, —S-aryl, —S-heterocyclyl, or —N(R4)R5;

m represents an integer from 0-10;

Q1, Q2 . . . Qs, each independently, represent —O or —N(R3);

X1, X2 . . . Xs, each independently, represent —O— or —N(R3)—;

$t_s$ is a constitutional unit of the polymeric chain;

the s of $t_s$ is an integer and at least 1 or more;

$n_1, n_2 \ldots n_s$ is greater than 0 to about 1000 or more;

x is an integer from 1 to about 1000 or more; and

M1, M2 . . . Ms each independently represent an aliphatic or aryl group.

3. The composition of claim 1, wherein R1 is represented by $$\text{Formula IIa}$$

$$*\left[\left(X_1\underset{Q_1}{\overset{\parallel}{M_1}}\right)_{n_1}^{t_1}\left(X_2\underset{Q_2}{\overset{\parallel}{M_2}}\right)_{n_2}^{t_2}\right]_x R_7$$

wherein

* represents the central phosphorus atom of Formula I;

R7 represents —O-alkyl, —O-cycloalkyl, —O-aryl, —O-heterocyclyl, —S-alkyl, —S-cyloalkyl, —S-aryl, —S-heterocyclyl, or —N(R4)R5;

m represents an integer from 0-10;

Q1 represents —O or —N(R3);

M1 and M2 each independently represent an aliphatic or aryl group;

X1 and X2 each independently, represent —O— or —N(R3)—;

x is an integer equal to at least 1 or more;

$n_1$ and $n_2$ are equal to 1; and the $t_1$ and $t_2$ units may be in any order for each occurrence of the unit x.

4. The composition of claim 1, wherein Q represents O.

5. The composition of claim 3, wherein M1 and M2 are each independently selected from the group consisting of —CH(CH$_3$)—; —CH(CH$_3$)CO$_2$CH(CH$_3$)—; —(CH$_2$)$_d$—; and
—(CH$_2$)$_d$—O—; wherein d is from 1 to about 12.

6. The composition of claim 2, wherein R7 is represented by —O-alkyl.

7. The composition of claim 3, wherein R7 is represented by —O-alkyl.

8. The composition of claim 7, wherein R2 is selected from the group consisting of —H, alkyl, cycloalkyl, —O-alkyl, and —O-cycloalkyl.

9. The composition of claim 1, wherein R1 is represented by:

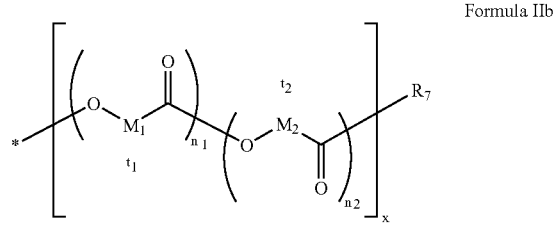

Formula IIb wherein
* represents the central phosphorus atom of Formula I;
M1 and M2 are each independently are selected from the group consisting of —CH(CH$_3$)—; —CH(CH$_3$)CO$_2$CH(CH$_3$)—; —(CH$_2$)$_d$—; and —(CH$_2$)$_d$—O—; wherein d is from 1 to about 12;
R7 is represented by —O-alkyl;
$n_1$ and $n_2$ are equal to 1;
the $t_1$ and $t_2$ units may be in any order for each occurrence of the unit x; and
x is an integer from 1 to about 20.

10. The composition of claim 1, wherein R1 is represented by

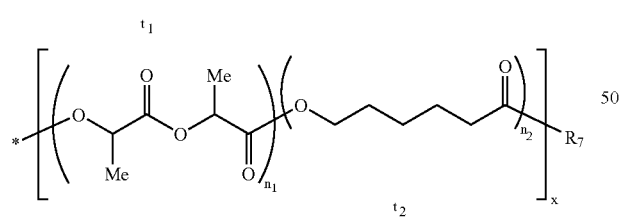

Formula IIc wherein
* represents the central phosphorus atom of Formula I;
R7 represents —O—(CH$_2$)$_m$CH$_3$ or —O—(CH$_2$CH$_2$O)$_m$CH$_3$, wherein m is at least 1;
$n_1$ and $n_2$ are on average for each polymeric chain in the compound equal to about 2 and 2 or about 5.5 and 1.8, respectively;
the $t_1$ and $t_2$ units may be in any order for each occurrence of the unit x; and
x is equal to 1.

11. The composition of claim 1, wherein R1 is

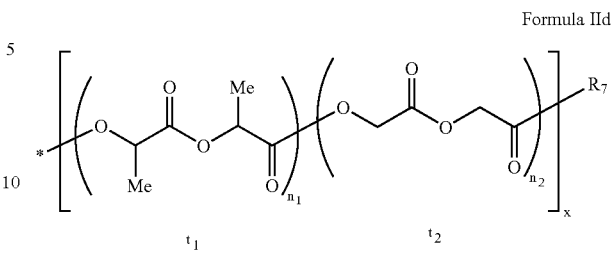

Formula IId wherein
* represents the central phosphorus atom of Formula I;
R7 represents —O—(CH$_2$)$_m$CH$_3$, wherein m is at least 1;
$n_1$ and $n_2$ are on average for each unit x are equal to about 2.4 and 1.6, respectively;
the $t_1$ and $t_2$ units may be in any order for each occurrence of the unit x; and
x is at least 1.

12. The composition of claim 9, wherein R2 is selected from the group consisting of —H, alkyl, cycloalkyl, —O-alkyl, and —O-cycloalkyl.

13. The composition of claim 1, wherein R1 is represented by:

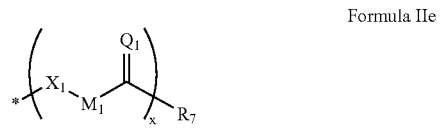

Formula IIe wherein
* represents the central phosphorus atom of Formula I;
M1 is selected from the group consisting of —CH(CH$_3$)—; —CH(CH$_3$)CO$_2$CH(CH$_3$)—;
—(CH$_2$)$_d$—; and —(CH$_2$)$_d$—O—; wherein d is from 1 to about 12;
Q1 represents —O or N(R3);
R7 represents —O—(CH$_2$)$_m$CH$_3$, wherein m is at least 1; and
x is an integer equal to at least 2.

14. The composition of claim 1, wherein R1 is represented by:

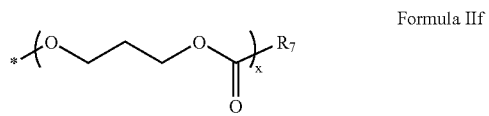

Formula IIf wherein
* represents the central phosphorus atom of Formula I;
R7 represents —O—(CH$_2$)$_m$CH$_3$, wherein m is at least 1, and x is at least 2.

15. The composition of claim 1, wherein said phosphorus-containing compound is amphiphilic.

16. The composition of claim 1, wherein said phosphorus-containing compound exhibits reverse thermal gelation.

17. The composition of claim 16, wherein said phosphorus-containing compound has a gelation temperature of below about 37° C.

18. The composition of claim 1, further comprising a therapeutic agent.

19. The composition of claim 9, further comprising a therapeutic agent.

20. A composition, comprising a phosphorus-containing compound with a star structure represented by the following formula:

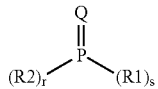

wherein, independently for each occurrence:

Q represents —O or —N(R3);

r represents 0 or 1, and s represents 3 or 2, such that r+s=3;

R2 represents —H, alkyl, cycloalkyl, —O-alkyl, —O-cycloalkyl, cycloalkenyl, —O-cycloalkenyl, aryl, —O-aryl, heterocycle, —O-heterocycle, polycycle, —O-polycycle, or —N(R4)R5;

R3 represents —H, alkyl, aryl, cycloalkyl, cycloalkenyl, heterocycle, or polycycle;

R4 and R5, each independently, represent a hydrogen, an alkyl, an alkenyl, —(CH2)$_m$—R6, or R4 and R5, taken together with the N atom to which they are attached complete a heterocycle having from 4 to about 8 atoms in the ring structure;

m represents an integer from 0-10; and

R6 represents —H, alkyl, cycloakyl, —O-alkyl, —O-cycloalkyl, cycloalkenyl, —O-cycloalkenyl, aryl, —O-aryl, heterocycle, —O-heterocycle, polycycle or —O-polycycle;

R1 comprises:

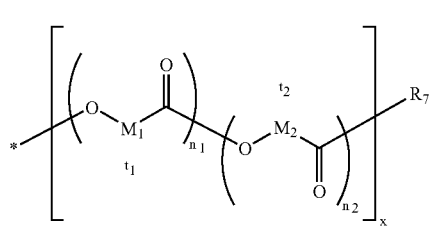

Formula IIb wherein

* represents the central phosphorus atom of Formula I;

M1 and M2 are each independently are selected from the group consisting of —CH(CH$_3$)—;

—CH(CH$_3$)CO$_2$CH(CH$_3$)—; —(CH$_2$)$_d$—; and —(CH$_2$)$_d$—O—; wherein d is from 1 to about 12;

R7 is represented by —O-alkyl;

n$_1$ and n$_2$ are equal to 1;

the t$_1$ and t$_2$ units may be in any order for each occurrence to the unit x; and x is an integer from 1 to about 20.

* * * * *